US007241873B2

(12) United States Patent
Uede et al.

(10) Patent No.: US 7,241,873 B2
(45) Date of Patent: Jul. 10, 2007

(54) RECOMBINANT ANTI-OSTEOPONTIN ANTIBODY AND USE THEREOF

(75) Inventors: Toshimitsu Uede, Hokkaido (JP); Shigeyuki Kon, Gunma (JP); Nobuchika Yamamoto, Osaka (JP); Hirofumi Higuchi, Kumamoto (JP); Masaharu Torikai, Kumamoto (JP); Yoshiyuki Tokieda, Kumamoto (JP); Toshihiro Nakashima, Kumamoto (JP); Hiroaki Maeda, Kumamoto (JP)

(73) Assignees: Juridical Foundation the Chemo-sero-therapeutic Research Institute, Kumamoto-shi (JP); Astellas Pharma Inc., Tokyo (JP)

( * ) Notice: Subject to any disclaimer, the term of this patent is extended or adjusted under 35 U.S.C. 154(b) by 153 days.

(21) Appl. No.: 10/489,866

(22) PCT Filed: Sep. 25, 2002

(86) PCT No.: PCT/JP02/09868

§ 371 (c)(1), (2), (4) Date: Mar. 24, 2004

(87) PCT Pub. No.: WO03/027151

PCT Pub. Date: Apr. 3, 2003

(65) Prior Publication Data

US 2006/0002923 A1 Jan. 5, 2006

(30) Foreign Application Priority Data

Sep. 25, 2001 (JP) ............................ 2001-290700

(51) Int. Cl.
*C07K 16/46* (2006.01)
*C07K 16/28* (2006.01)

(52) U.S. Cl. ............................. 530/387.3; 530/388.24

(58) Field of Classification Search ..................... None
See application file for complete search history.

(56) References Cited

U.S. PATENT DOCUMENTS

| | | | | |
|---|---|---|---|---|
| 6,632,927 | B2 * | 10/2003 | Adair et al. | 530/387.3 |
| 2002/0188962 | A1 | 12/2002 | Denhardt et al. | |
| 2004/0234524 | A1 | 11/2004 | Uede et al. | |
| 2006/0002923 | A1 | 1/2006 | Uede et al. | |

FOREIGN PATENT DOCUMENTS

| | | |
|---|---|---|
| EP | 0 125 023 | 11/1984 |
| EP | 239 400 | 9/1987 |
| EP | 0705 842 A2 | 4/1996 |
| EP | 0 921 189 A1 * | 11/1998 |
| EP | 1 408 113 | 4/2004 |
| WO | WO 90/07861 | 7/1990 |
| WO | WO 94/20632 | 9/1994 |
| WO | WO 95/28426 | 10/1995 |
| WO | WO 98/07750 | 2/1998 |
| WO | WO 98/08379 | 3/1998 |
| WO | WO 98/56405 | 12/1998 |
| WO | WO 99/08730 | 2/1999 |
| WO | 00 63247 | 10/2000 |
| WO | WO 00/63241 | 10/2000 |
| WO | 01/71358 | 9/2001 |
| WO | W 02/32940 A2 | 4/2002 |
| WO | WO 03/046135 A2 | 6/2003 |

OTHER PUBLICATIONS

Rudikoff et al Single amino acid substitution altering antigen-binding specificity. Proc Natl Acad Sci U S A. Mar. 1982;79(6):1979-83.*
Panka et al. Variable region framework differences result in decreased or increased affinity of variant anti-digoxin antibodies. Proc Natl Acad Sci U S A. 85(9):3080-3084, 1988.*
Bautista et al Inhibition of Arg-Gly-Asp (RGD)-mediated cell adhesion to osteopontin by a monoclonal antibody against osteopontin. J Biol Chem. Sep. 16, 1994;269(37):23280-5.*
Shigeyuki Kon, et al., "Mapping of functional epitopes of osteopontin by monoclonal antibodies raised against defined internal sequences", Journal of Cellular Biochemistry, vol. 84, No. 2, pp. 420-432 2002.
Peter T. Jones, et al., "Replacing the complementarity-determining regions in a human antibody with those from a mouse", NATURE, vol. 321, pp. 522-525 May 29, 1986.
Diosdado S. Bautista, et al., "Inhibition of Arg-Gly-Asp (RGD)-mediated cell adhesion to osteopontin by a monoclonal antibody against osteopontin", The Journal of Biological Chemistry, vol. 269, No. 37, pp. 23280-23285 Sep. 16, 1994.
Yoshiki Saitoh, et al., Laboratory Investigation, vol. 72, No. 1, pp. 55-63 1995.
Yasuyuki Yokosaki, et al., The Journal of Biological Chemistry, vol. 274, No. 51, pp. 36328-36334 Dec. 17, 1999.
Philip M. Greeen, et al., FEBS Letters, vol. 503, pp. 75-79 2001.
J. R. Waller, et al., British Journal of Surgery, vol. 88, pp. 1429-1441 2001.
Satu R. K. Lehtonen, et al., Transplantation, vol. 72, No. 6, pp. 1138-1144 Sep. 27, 2001.
Anthony O'Regan, et al., Int.J.Exp. Path, vol. 81, pp. 373-390 2000.
Kayla J. Bayless, et al., The Journal of Biological Chemistry, vol. 276, No. 16, pp. 13483-13489 Apr. 20, 2001.

(Continued)

*Primary Examiner*—Maher M. Haddad
(74) *Attorney, Agent, or Firm*—Oblon, Spivak, McClelland, Maier & Neustadt, P.C.

(57) ABSTRACT

A recombinant antibody in which at least the constant regions in the heavy chain and the light chain have been converted into human-origin regions and which inhibits the binding of an integrin recognizing the RGD sequence to osteopontin or its fragment and inhibits the binding of an integrin recognizing the SVVYGLR sequence or a sequence corresponding thereto to osteopontin or its fragment. This antibody is useful as a remedy for autoimmune diseases and a remedy for rheumatism or rheumatoid arthritis. Thus, a method of treating autoimmune diseases, rheumatism or rheumatoid arthritis is provided. This osteopontin antibody is useful in a diagnostic for rheumatism and a method of diagnosing rheumatism too.

7 Claims, 17 Drawing Sheets

OTHER PUBLICATIONS

Yasuyuki Taooka, et al., The Journal of Cell Biology, vol. 145, No. 2, pp. 413-420 Apr. 19, 1999.

Inhibitory Effects of MLDG-containing Heterodimeric Disintegrins Reveal Distinct Structural Requirements for Interaction of the Integrin α9β1 with VCAM-1, Tenascin-C, and Osteopontin, Cesary marcinkiewics, et al. , The Journal of Biological Chem., Oct. 13, 2000, vol. 275, No. 41, pp. 31930-31937.

Mapping of the Cryptic Integrin-Binding Site in Osteopontin Suggests a New Mechanism by Which Thrombin Can Regulate Inflammation and Tissue Repair, Yasuyuki Yokasaki, et al. Trends Cardiovasc Med. vol. 10, No. 4, 2000 pp. 155-159.

Osteopontin as a means to cope with environmental insults: regulation of inflammation, tissue remodeling, and cell survival, David T. Denhardts, et al., The Journal of Clinical Investigation, May 2001, vol. 107, No. 9, pp. 1055-1061.

Mice Lacking Osteopontin Show Normal Development and Bone Structure but Display Altered osteoclast Formation In Vitro, Susan R. Rittling, et al. Journal of Bone and Mineral Research, vol. 13, No. 7, 1998, pp. 1101-1111.

Eta-1 (Osteopontin): An Early Component of Type-1 (Cell Mediated) Immunity, Samy Ashkar, et al. Science, Feb. 4, 2000, vol. 287, pp. 860-364.

Antibodies to Different Peptides in Osteopontin Reveal Complexities in the Various Secreted Forms, Shigeyuki Kon, et al. Journal of Cellular Biochemistry , 2000, 77, pp. 487-498.

Osteopontin deficiency protects joints against destruction in anti-type II collagen antibody-induced arthritis in mice, Kenji Yamoto, et al. PNAS, vol. 99, No. 7, pp. 4556-4561.

Enhanced Local Production of Osteopontin in Rheumatoid Joints, Shiro Ohshima, et al., The Journal of Rheumatogoty 2002, vol. 29, No. 10, pp. 2061-2067.

The Third Annual Meeting of Osteopontin Study Group, May 27, 2000 (with English translation of related sections).

The Fourth Annual Meeting of Osteopontin Study Group, Jun. 9, 2001 (with English translations of related sections).

Analysis of the α4β Integrin-Osteopontin Interaction, Simon T. Barry, et al., Experimental Cell Research, 2000, 258, pp. 342-351.

Chromic Allograft Nephropathy—Biopsy Findings and Outcome, Poul Freese, et al., Nephrol Dial Transplant, 2001, 16, pp. 2001-2406.

Samy Ashkar, et al., "Eta-1 (Osteopontin): An Early Component of Type-1 (Cell-Mediated) Immunity", Science, vol. 287, Feb. 4, 2000, pp. 860-864.

Dorothee Chabas, et al., "The Influence of the Proinflammatory Cytokine, Osteopontin, on Autoimmune Demyelinating Disease", Science, vol. 294, Nov. 23, 2001, pp. 1731-1735.

Marianne Jansson, et al., "Cutting Edge: Attenuated Experimental Autoimmune Encephalomyelitis in Eta-1/Osteopontin-Deficient Mice[1]", The American Association of Immunologists, 2002, pp. 2096-2099.

Mukundan G. Attur, et al., "Osteopontin an Intrinsic Inhibitor of Inflammation in Cartilage", Regulation of NO and $PGE_2$ by Osteopontin, pp. 578-584.

Butista, D.S. et al. "A Monoclonal Antibody against Osteopontin Inhibitis RGD-Mediated Cell Adhesion to Osteopontin", Annals of the New York Academy of Sciences, vol. 760, pp. 309-311, XP009033073 1995.

Hotta, Hiroshi et al. "Detection of Various Epitopes of Murine Osteopontin by Monoclonal Antibodies", Biochemical and Biophysical Research Communications, vol. 257, pp. 6-11, XP002286858.

Rittling, Susan R. et al. "Detection of Mouse Osteopontin by Western Blotting", Biochemical and Biophysical Research Communications, vol. 250, pp. 287-292, XP002286859.

Sakata, Masahiro et al. "Autoantibodies to Osteopontin in Patients with Osteoarthritis and Rheumatoid Arthritis". The Journal of Rheumatology, vol. 28, No. 7, pp. 1492-1495, XP009033062.

Petrow, Peter K. et al. "Expression of Osteopontin Messenger RNA and Protein in Rheumatoid Arthritis", Arthritis & Rheumatism, vol. 43, No. 7, pp. 1597-1605, XP009033184 2000.

* cited by examiner

Fig. 2
A
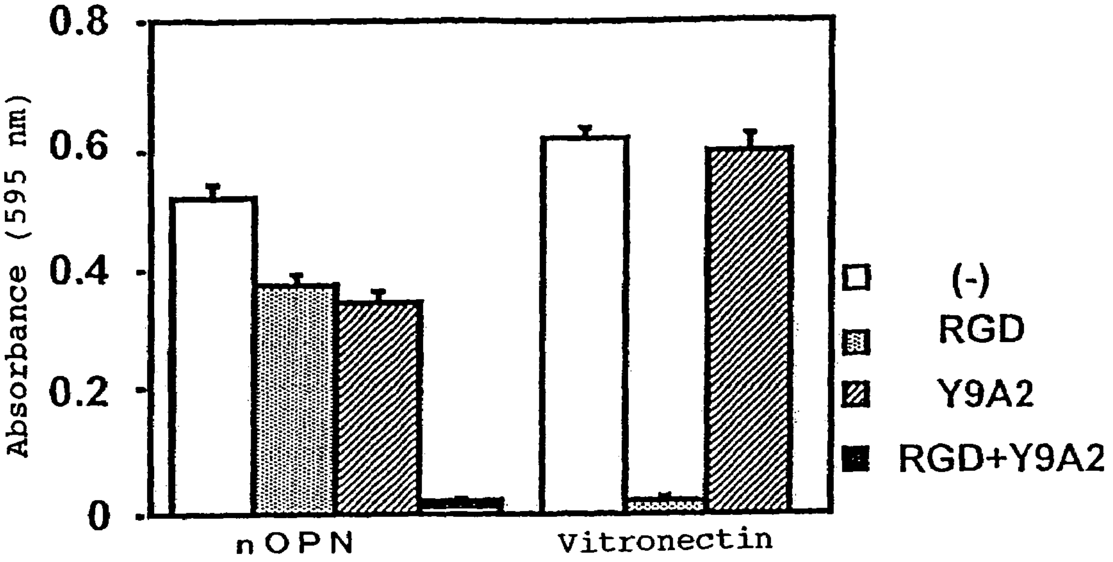
B
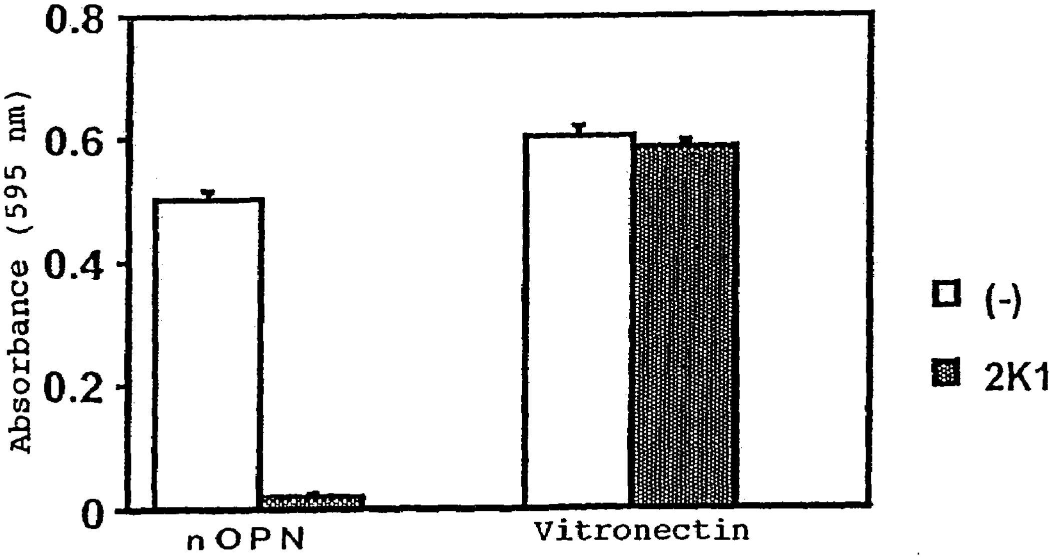

Fig. 7

```
                          FR1                    | CDR1 |        FR2       |      CDR2
                 10        20        30        40        50        60
2K1-VH   QVQLQQSGAE LVRPGASVKL SCKALGYTFT DYEMHWVKQT PVHGLEWIGA IHPGRGGTAY
DP-88    QVQLvQSGAE vkkPGsSVKv SCKAsGgTFs sYaisWVrQa PgqGLEWmGg IiPifGtanY

             |             FR3                   |   CDR3   |      FR4
                 70        80        90        100        110
2K1-VH   NQKFKGKATL TADKSSSTAY MELSSLTSED SAVYYCTRIT GYF--DVWGAGT TVTVSS
DP-88    aQKFqGrvTI TADKStSTAY MELSSLrSED tAVYYCaRyy yYygmDVWGqGT TVTVSS
                                                              JH 6
```

Fig. 8

```
                 FR1         |     CDR1     |     FR2     | CDR2
                10         20         30         40         50         60
2K1-VL   DVLMTQTPLS LPVSLGDQAS ISCRSSQSIV HSN-GNTYLEW YLQKPGQSPK LLIYKVSNRF
DPK13    DivMTQTPLS LPVtpGepAS ISCRSSQSll dSddGNTYLdW YLQKPGQSPq LLIYtlSyRa
DPK18    DVvMTQsPLS LPVtLGqpAS ISCRSSQSlV ySd-GNTYLnW fqQrPGQSPr rLIYKVSNRd

         |             FR3              | CDR3  |    FR4
                70         80         90         100        110
2K1-VL   SGVPDRFSGS GSGTDFTLKI SRVEAEDLGV YYCFQGSHVP LTFGAGTKLE LKR
DPK13    SGVPDRFSGS GSGTDFTLKI SRVEAEDvGV YYCmQriefP yTFGqGTKLE iKR
DPK18    SGVPDRFSGS GSGTDFTLKI SRVEAEDvGV YYCmQGtHwP yTFGqGTKLE iKR
                                                     Jκ 2
```

Fig. 9

```
          10        20        30        40        50        60
CACGAAGCTTGCCGCCACCATGGACTGGACCTGGCGCGTGTTTTGCCTGCTCGCCGTGGC
 HindIII            M  D  W  T  W  R  V  F  C  L  L  A  V  A

          70        80        90       100       110       120
TCCTGGGGCCCACAGCCAGGTGCAGCTGGTGCAGTCTGGGGCTGAGGTGAAGAAGCCTGG
 P  G  A  H  S  Q  V  Q  L  V  Q  S  G  A  E  V  K  K  P  G

         130       140       150       160       170       180
GTCCTCCGTGAAGGTCTCCTGCAAGGCTTCTGGAGGTACCTTCAGCGACTATGAAATGCA
 S  S  V  K  V  S  C  K  A  S  G  G  T  F  S  D  Y  E  M  H

         190       200       210       220       230       240
CTGGGTGCGACAGGCCCCTGGACAAGGGCTTGAGTGGATGGGAGCTATTCATCCAGGAAG
 W  V  R  Q  A  P  G  Q  G  L  E  W  M  G  A  I  H  P  G  R

         250       260       270       280       290       300
AGGTGGTACTGCCTACAATCAGAAGTTCAAGGGCAGAGTCACGATTACCGCGGACAAATC
 G  G  T  A  Y  N  Q  K  F  K  G  R  V  T  I  T  A  D  K  S

         310       320       330       340       350       360
CACTAGTACAGCCTACATGGAGCTGAGCAGCCTGAGATCTGAGGACACGGCCGTGTATTA
 T  S  T  A  Y  M  E  L  S  S  L  R  S  E  D  T  A  V  Y  Y

         370       380       390       400       410       420
CTGTGCGAGAATTACTGGGTACTTCGATGTCTGGGGGCAAGGGACCACGGTCACCGTCTC
 C  A  R  I  T  G  Y  F  D  V  W  G  Q  G  T  T  V  T  V  S

         430       440
CTCAGGTGAGTGGATCCGCGA
 S              BamHI
```

Fig. 10

```
        10         20         30         40         50         60
CACGAAGCTTGCCGCCACCATGGGATGGAGCTGTATCATCCTCTTCTTGGTAGCAACAGC
   HindIII         M  G  W  S  C  I  I  L  F  L  V  A  T  A

        70         80         90        100        110        120
TACAGGTGTCCACTCCGATGTTGTGATGACTCAGTCTCCACTCTCCCTGCCCGTCACCCT
 T  G  V  H  S  D  V  V  M  T  Q  S  P  L  S  L  P  V  T  L

       130        140        150        160        170        180
TGGACAGCCGGCCTCCATCTCCTGCAGGAGCTCTCAAAGCATTGTACATAGTAATGGAAA
 G  Q  P  A  S  I  S  C  R  S  S  Q  S  I  V  H  S  N  G  N

       190        200        210        220        230        240
CACCTATTTGGAATGGTACCTGCAGAAGCCAGGGCAGTCTCCACAGCTCCTGATCTATAA
 T  Y  L  E  W  Y  L  Q  K  P  G  Q  S  P  Q  L  L  I  Y  K

       250        260        270        280        290        300
AGTTTCCAACCGATTTTCTGGGGTCCCAGACAGATTCAGCGGCAGTGGGTCAGGCACTGA
 V  S  N  R  F  S  G  V  P  D  R  F  S  G  S  G  S  G  T  D

       310        320        330        340        350        360
TTTCACACTGAAAATCAGCAGGGTTGAAGCTGAAGACGTCGGAGTTTATTACTGCTTTCA
 F  T  L  K  I  S  R  V  E  A  E  D  V  G  V  Y  Y  C  F  Q

       370        380        390        400        410        420
AGGTTCACATGTTCCGCTCACGTTTGGCCAGGGGACCAAGCTGGAGATCAAACGTGAGTA
 G  S  H  V  P  L  T  F  G  Q  G  T  K  L  E  I  K  R

       430        440        450
GAATTTAAACTTTGCTTCCTCAGTTGGATCCGCGA
                            BamHI
```

Fig. 11

```
             10         20         30         40         50         60
5'-CACGAAGCTT GCCGCCACCA TGGACTGGAC CTGGCGCGTG TTTTGCCTGC TCGCCGTGGC

             70         80         90        100        110        120
   TCCTGGGGCC CACAGCCAGG TGCAGCTGGT GCAGTCT-3'
                     3'-ACGTCGACCA CGTCAGACCC CGACTCCACT TCTTCGGACC

            130        140        150        160        170        180
   CAGGAGGCAC TTCCAGAGGA CGTTCCGAAG ACCTCCATGG AAGTCGCT-5'
                               5'-TTC TGGAGGTACC TTCAGCGACT ATGAAATGCA

            190        200        210        220        230        240
   CTGGGTGCGA CAGGCCCCTG GACAAGGGCT TGAGTGGATG GGAGCTATTC ATCCAGGAAG
                                                      3'-G TAGGTCCTTC

            250        260        270        280        290        300
   AGGTGGTACT-3'
   TCCACCATGA CGGATGTTAG TCTTCAAGTT CCCGTCTCAG TGCTAATGGC GCCTGTTTAG
                                                                5'-TC

            310        320        330        340        350        360
   GTGATCATGT CGGATGTAC-5'
   CACTAGTACA GCCTACATGG AGCTGAGCAG CCTGAGATCT GAGGACACGG CCGTGTATTA

            370        380        390        400        410        420
   CTGTGCGAGA ATTACTGGGT ACTTCGATGT CTG-3'
           3'-ATGACCCA TGAAGCTACA GACCCCCGTT CCCTGGTGCC AGTGGCAGAG

            430        440
   GAGTCCACTC ACCTAGGCGC T-5'
```

Fig. 12

```
            10         20         30         40         50         60
5'-CACGAAGCTT GCCGCCACCA TGGGATGGAG CTGTATCATC CTCTTCTTGG TAGCAACAGC

            70         80         90        100        110        120
   TACAGGTGTC CACTCCGATG TT-3'
 3'-TGTCCACAG GTGAGGCTAC AACACTACTG AGTCAGAGGT GAGAGGGACG GGCAGTGGGA

           130        140        150        160        170        180
   ACCTGTCGGC CGGAGGTAGA GGACGTCCTC GAGAGTTTCG TAA-5'
                       5'-TGCAGGAG CTCTCAAAGC ATTGTACATA GTAATGGAAA

           190        200        210        220        230        240
   CACCTATTTG GAATGGTACC TGCAGAAGCC AGGGCAGTCT CCACAGCTCC TGATCTATAA
                                                     3'-G ACTAGATATT

           250        260        270        280        290        300
   AGTTTCCAAC CGATT-3'
   TCAAAGGTTG GCTAAAAGAC CCCAGGGTCT GTCTAAGTCG CCGTCACCCA GTCCGTGACT

           310        320        330        340        350        360
   AAAGTGTGAC TTTTAGTCGT CCCAACTTCG ACTTCTGCAG CCT-5'
                       5'-GTTGAAGC TGAAGACGTC GGAGTTTATT ACTGCTTTCA

           370        380        390        400        410        420
   AGGTTCACAT GTTCCGCTCA CGTTTG-3'
     3'-GTGTA CAAGGCGAGT GCAAACCGGT CCCCTGGTTC GACCTCTAGT TTGCACTCAT

           430        440        450
   CTTAAATTTG AAACGAAGGA GTCAACCTAG GCGCT-5'
```

RECOMBINANT ANTI-OSTEOPONTIN ANTIBODY AND USE THEREOF

CROSS-REFERENCE TO RELATED APPLICATIONS

This application is a national-stage filing of PCT/JP02/09868, filed Sep. 25, 2002. It claims priority to Japan 2001-290700, filed Sep. 25, 2001.

TECHNICAL FIELD OF THE INVENTION

The present invention relates to a recombinant anti-osteopontin antibody and a method for therapeutically treating autoimmune diseases, rheumatism and rheumatoid arthritis, using the antibody.

BACKGROUND ART

Osteopontin (referred to as "OPN" hereinbelow) is an acidic, calcium-binding glycoprotein abundant in bone. It has been known that three types of human OPN isoforms namely osteopontin-a (referred to as "OPN-a" hereinbelow), osteopontin-b (referred to as "OPN-b" hereinbelow) and osteopontin-c (referred to as "OPN-c" hereinbelow) are naturally generated by alternative splicing (Y. Saitoh et al., (1995): Laboratory Investigation, 72, 55–63). It has been believed that among them, the precursor of OPN-a has an amino acid sequence shown below as SEQ ID NO. 1 in the Sequence Listing, where the signal peptide is cleaved on secretion, so that the mature form OPN-a of I17-N314 is prepared. Additionally, the mature OPN is cleaved at the C-terminal side of the 168-th residue arginine with thrombin in a biological organism into two fragments, namely N-terminal and C-terminal fragments.

OPN described above has various physiologically, pathologically significant functions, for example cell adhesion, cell migration, tumorigenesis, immune response and inhibition of complement-mediated cytolysis. Various types of receptors on cellular surface mediate the various functions. OPN has the RGD sequence therein (for example, OPN-a has the sequence from the residue at position 159 to the residue at position 161). Integrin species recognizing the RGD sequence such as $\alpha V\beta 3$, $\alpha V\beta 1$ and $\alpha V\beta 5$ are major OPN receptors; specifically, the integrin species $\alpha V\beta 3$, $\alpha V\beta 1$ and $\alpha V\beta 5$ mediate cell adhesion in vascular smooth muscle cells. Further, $\alpha V\beta 3$ is involved in the migrations of macrophages, lymphocytes, endothelial cells, and smooth muscle cells and the like.

Further, research works so far have elucidated that OPN also binds through the sequence SVVYGLR (residues 11–17 of SEQ ID NO: 1) to $\alpha 9\beta 1$, $\alpha 4\beta 1$ and $\alpha 4\beta 7$ integrin species and that a difference in the mode is also found such that $\alpha 4\beta 1$ binds to both OPN not yet cleaved with thrombin (non-cleavage-type OPN) and the N-terminal fragment of thrombin-cleaved OPN (cleavage-type OPN), while $\alpha 9\beta 1$ binds only to the thrombin-cleavage-type OPN. (Y. Yokosaki et al., (1999): The Journal of Biological Chemistry 274, 36328–36334/P. M. Green et al., (2001): FEBS Letters 503, 75–79/S. T. Barry et al., (2000): Experimental Cell Research 258, 342–351). These integrin subunits $\alpha 9$ and $\alpha 4$ or the integrin subunits $\beta 1$ and $\beta 7$ are highly similar in terms of amino acid sequence to each other. Additionally, the integrin species $\alpha 4\beta 1$ and $\alpha 4\beta 7$ are mainly found in lymphocytes and monocytes, while in neutrophils, the integrin species are expressed very slightly. Alternatively, $\alpha 9\beta 1$ is highly expressed selectively in neutrophils and has functions essential for neutrophil migration through VCAM-1 and Tenascin-C. Additionally, the integrin is also expressed diversely in muscular cells, epithelial cells and liver cells and the like. As described above, the cytoplasm domains of the integrin subunits $\alpha 4$ and $\alpha 9$ cooperatively promote leukocyte migration toward inflammatory sites and aggregation therein, via individual cellular signal transmission pathways subtly differing from each other, to enhance their infiltration activities. In such manner, the integrin subunits are involved in various inflammatory reactions.

As described above, various types of integrin species promote leukocyte migration and are thus involved in inflammatory reactions. Therefore, pharmaceutical substances inhibiting these integrin activities may have a potential usefulness as an anti-inflammatory agent. For example, the integrin $\alpha V\beta 3$ is expressed in osteoclast cells, vascular endothelial cells and smooth muscle cells and the like. An anti-$\alpha V\beta 3$ antibody is now under way of development, which will work to inhibit the binding between the integrin $\alpha V\beta 3$ and various binding ligands thereof to potentially exert for example an action to suppress articular damages.

Because receptors of the integrin family commonly emerge in diverse tissues to provide essential functions for the control of vital activities, however, the use of antibodies against integrin for the therapeutic treatment of rheumatoid arthritis and osteoarthritis may possibly elicit the same inhibition at other sites and may also cause the occurrence of side effects.

Additionally, WO 01/71358 discloses a screening method for a substance inhibiting the binding between the $\alpha 4$ integrin and osteopontin and a method for therapeutically treating inflammatory diseases, using the substance recovered by such screening.

Various factors have been indicated for the pathogenesis of rheumatoid arthritis. Thus, many reports have been issued therefor. However, not any of them is reliable. Further, currently known therapeutic methods thereof are nosotropic and have not been essentially satisfactory.

Hence, it has been strongly desired to definitely elucidate the pathogenesis of rheumatoid arthritis and provide a more excellent therapeutic method thereof. It is an object of the invention to solve such problems.

Further, rheumatoid arthritis is hardly discriminated from osteoarthritis. Therefore, it is an additional object of the invention to provide a diagnostic method thereof.

The inventors found that the OPN concentration in the articular cavity fluids of rheumatism patients and osteoarthritis patients was at a higher value. Additionally, the inventors found the increase of the ratio of the N-terminal fragment of the thrombin-cleavage type in the total OPN in rheumatism patients for the first time. Thus, the inventors speculated that OPN might be deeply involved in the onset of these diseases. Then, the inventors verified the findings at experiments using OPN knockout mice.

Further, the inventors prepared antibodies individually recognizing the N-terminal fragment and the C-terminal fragment discriminatively from the thrombin-cleaved OPN. Then, the inventors found at experiments using them that the N-terminal fragment of the thrombin-cleaved OPN was at a high concentration in the articular cavity fluids of patients with rheumatoid arthritis, in particular.

Still further, the inventors focused their attention to the fact that the N-terminal fragment of high concentration is observed in the case of the patients with rheumatoid arthritis, and the fragment contains both the RGD and the SVVYGLR (residues 11–17 of SEQ ID NO: 1) sequence sites capable of being recognized by human-type integrin. Then, the inventors anticipated that an antibody capable of blocking both the sequence sites simultaneously would inhibit the binding between OPN and integrin so broadly that the antibody could be effective for the therapeutic treatment of rheumatoid arthritis and osteoarthritis.

Further, OPN is distributed in kidney, placenta, ovary, brain, skin and the like, but is mainly expressed in bone tissue. The inventors considered that for the therapeutic treatment of rheumatoid arthritis, the binding between OPN and integrin would preferably be blocked by a method more specific to the OPN side. Because the diverse integrin species might be involved in inflammation in a cooperative manner, then, the inventors considered that it would be effective to more broadly block the binding to these diverse integrin species.

Therefore, the inventors prepared an antibody which can inhibit the binding between the RGD sequence site of human OPN and integrin and also the binding between the SVVYGLR (residues 11–17 of SEQ ID NO: 1) sequence site of human OPN and integrin, and then verified the effects thereof at experiments for cell adhesion and cell migration and the like. Further, the inventors recovered an antibody against a synthetic peptide corresponding to the inner sequence of murine OPN, to examine the efficacy of such antibody as a therapeutic agent, using an arthritis-diseased model in mouse.

More specifically, because murine OPN has the sequences RGD and SLAYGLR (SEQ ID NO: 52) recognizable by murine integrin, which are located at positions homologous to human OPN in terms of amino acid sequence, an antibody M5 was recovered as an antibody simultaneously blocking these sequences. It was verified that the binding of the antibody M5 with murine OPN and the thrombin digestion products thereof was inhibited by the peptide GRGDSP (SEQ ID NO: 55) including the sequence RGD and that the antibody M5 inhibited the migration of TNF-α-activated monocyte derived from murine spleen. It was also observed that the antibody M5 had an action to suppress bone damage when examined in a murine calvaria organ culture system. Further, it was confirmed that the antibody had an apparent therapeutic effect when administered to a murine collagen arthritis model.

The aforementioned results strongly suggest that the antibody, which can simultaneously block the binding of the RGD and SVVYGLR (residues 11–17 of SEQ ID NO: 1) sequence sites with human-type integrin, can inhibit the binding between OPN and integrin so as to be effective for the therapeutic treatment of rheumatoid arthritis and the like. Furthermore, the results suggest that the antibody can possibly be effective not only for rheumatism such as juvenile articular rheumatism and chronic rheumatism but also for psoriatic arthritis and psoriasis. Furthermore, chronic rejections after organ transplantation are characterized by complication with vascular and bronchial occlusive disorders. The results of histological examinations thereof suggest that activation of T cell and macrophage triggers generation of cytokine and growth factors, leading to disorders of vascular endothelial cell and proliferation of vascular smooth muscle cell which may lead to, via fibrogenesis and the like, vascular occlusion (P. Freese et al., (2001): Nephrol Dial Transplant, 16, 2401–2406/J. R. Waller et al., (2001): British Journal of Surgery, 88, 1429–1441/S. R. Lehtonen et al., (2001): Transplantation, 72, 1138–1144). And it is reported that OPN has an essential function for macrophage activation and fibrogenesis of vascular smooth muscle cell (A. O'Regan et al., (2000): Int J Exp Pathol, 81, 373–390). Thus, the OPN inhibitory antibody of the invention suppresses the migration of monocyte and neutrophil, thereby possibly suppressing a process toward such fibrogenesis. Thus, the antibody suppresses chronic rejections after organ transplantation, with the resultant contributions to organ adhesion. Additionally, the antibody will be effective for the therapeutic treatment of autoimmune diseases including systemic autoimmune diseases, erythematosus, uveitis, Behcet disease, multiple myositis, skein proliferative nephritis, sarcoidosis and the like.

Based on the above mentioned findings, the inventors found an anti-osteopontin antibody, which can inhibit the binding between an integrin recognizing the site of the amino acid sequence RGD and osteopontin or a fragment thereof, and can also inhibit the binding between an integrin recognizing the site of the amino acid sequence SVVYGLR (residues 11–17 of SEQ ID NO: 1) or a corresponding sequence thereto and osteopontin or a fragment thereof. The inventors filed an international application (PCT/JP02/03382) about the antibody.

DISCLOSURE OF THE INVENTION

The anti-osteopontin antibody is an antibody derived from mouse (referred to as "murine antibody" hereinafter) and has a high level of affinity with human osteopontin, to inhibit the peripheral monocyte or neutrophil migration activity of osteopontin. It is thus expected that the murine antibody can be utilized as a therapeutic agent of various inflammatory diseases mainly including human rheumatoid. However, administration of the murine antibody to humans has difficulties with unsafe profile such as antigenicity induction and the inefficacy of the protein with its half-life reduced, as far as a mouse-derived antibody is used.

Therefore, the inventors modified the murine antibody without detriment to its activity in a genetic engineering manner, and finally got the anti-osteopontin antibody with reduced induction of problematic antigenicity. In other words, the invention provides the following embodiments [1.] through [45.].

[1.] An anti-osteopontin antibody or an antibody fragment derived therefrom, wherein said antibody can inhibit the binding between an integrin recognizing the site of amino acid sequence RGD and osteopontin or a fragment thereof, and can also inhibit the binding between an integrin recognizing the site of amino acid sequence SVVYGLR (residues 11–17 of SEQ ID NO: 1) and osteopontin or a fragment thereof.

[2.] An anti-osteopontin antibody according to [1.], wherein said antibody is raised against a peptide containing a partial amino acid sequence RGDSVVYGLRS (residues 8–18 SEQ ID NO: 1) as the antigen.

[3.] An anti-osteopontin antibody according to [1.] or [2.], wherein said antibody is raised against the peptide VDTYDGRGDSVVYGLRS (residues 2–18 of SEQ ID NO: 1) as the antigen.

[4.] An anti-osteopontin antibody according to any one of [1.]–[3.], wherein said antibody is a monoclonal antibody.

[5.] An anti-osteopontin antibody according to any one of embodiments [1.]–[3.], wherein said antibody is a chimera antibody.

[6.] An anti-osteopontin antibody according to [5.], wherein said antibody has the following heavy chain (a) and the following light chain (b):

(a) a heavy chain comprising a mouse-derived heavy chain variable region and a human-derived heavy chain constant region; and (b) a light chain comprising a mouse-derived light chain variable region and a human-derived light chain constant region.

[7.] An anti-osteopontin antibody according to [5.] or [6.], characterized in that the mouse-derived heavy chain variable region in the heavy chain (a) has the amino acid sequence set forth in SEQ ID NO: 19.

[8.] An anti-osteopontin antibody according to [5.] or [6.], characterized in that the mouse-derived light chain variable region in the light chain (b) has the amino acid sequence set forth in SEQ ID NO: 20.

[9.] An anti-osteopontin antibody according to [5.] or [6.], wherein the heavy chain constant region in the heavy chain (a) is human Igγ1.

[10.] An anti-osteopontin antibody according to [5.] or [6.], wherein the light chain constant region in the light chain (b) is human Igκ.

[11.] An anti-osteopontin antibody according to any one of embodiments [1.]–[3.], wherein said antibody is a humanized antibody.

[12.]. An anti-osteopontin antibody according to [11.], wherein said anti-osteopontin antibody has the following heavy chain (c) and the following light chain (d):

(c) a heavy chain comprising a heavy chain variable region and a human-derived heavy chain constant region, wherein said heavy chain variable region is composed of the complementarity determining region derived from a mouse-derived heavy chain variable region and the framework region derived from a human-derived heavy chain variable region (d) a light chain comprising a light chain variable region and a human-derived light chain constant region, wherein said light chain variable region is composed of the complementarity determining region derived from a mouse-derived light chain variable region and the frame work region derived from a human-derived light chain variable region

[13.]. An anti-osteopontin antibody according to [11.] or [12.], characterized in that the complementarity determining region in the mouse-derived heavy chain variable region in the heavy chain (c) is an amino acid sequence selected from the group consisting of SEQ ID NOS: 21–23.

[14.] An anti-osteopontin antibody according to [11.] or [12.], characterized in that the complementarity determining region in the mouse-derived light chain variable region in the light chain (d) has an amino acid sequence selected from the group consisting of SEQ ID Nos. 24–26.

[15.] An anti-osteopontin antibody according to [11.] or [12.], characterized in that the heavy chain variable region in the heavy chain (c) is the amino acid sequence set forth in SEQ ID NO: 28.

[16.] An anti-osteopontin antibody according to [11.] or [12.], characterized in that the light chain variable region in the light chain (d) is the amino acid sequence set forth in SEQ ID NO: 30.

[17.] An anti-osteopontin antibody according to [11.] or [12.], wherein the heavy chain constant region in the heavy chain (c) is human Igγ1.

[18.] An anti-osteopontin antibody according to [11.] or [12.], wherein the light chain constant region in the light chain (d) is human Igκ.

[19.] A nucleotide sequence encoding the amino acid sequence set forth in SEQ ID NO: 19.

[20.] A nucleotide sequence encoding the amino acid sequence set forth in SEQ ID NO: 20.

[21.] A nucleotide sequence encoding the amino acid sequence set forth in SEQ ID NO: 28.

[22.] A nucleotide sequence encoding the amino acid sequence set forth in SEQ ID NO: 30.

[23.] A vector comprising a nucleotide sequence according to [19.] and the human Igγ1 gene sequence.

[24.] A vector comprising a nucleotide sequence according to [20.] and the human Igκ gene sequence.

[25.] A vector comprising a nucleotide sequence according to [21.] and the human Igγ1 gene sequence.

[26.] A vector comprising a nucleotide sequence according to [22.] and the human Igκ gene sequence.

[27.] A host cell transformed with vectors according to [23.] and [24.].

[28.] A host cell transformed with vectors according to [25.] and [26.].

[29.] A method for producing an anti-osteopontin chimera antibody according to [5.] or [6.], characterized in culturing a host cell according to [27.] and collecting said antibody from the liquid culture.

[30.] A method for producing an anti-osteopontin humanized antibody according to [11.] or [12.], characterized in culturing a host cell according to [28.] and collecting said antibody from the liquid culture.

[31.] A therapeutic agent for autoimmune diseases, wherein said therapeutic agent comprising an antibody according to any one of [1.]–[6.], [11.] or [12.] or an antibody fragment derived therefrom as effective ingredients.

[32.] A therapeutic agent for rheumatism, wherein said therapeutic agent containing an antibody according to any one of [1.]–[6.], [11.] or [12.] or an antibody fragment derived therefrom as effective ingredients.

[33.] A therapeutic agent for rheumatoid arthritis, wherein said therapeutic agent comprising an antibody according to any one of [1.]–[6.], [11.] or [12.] or an antibody fragment derived therefrom as effective ingredients.

[34.] A therapeutic agent for osteoarthritis, wherein said therapeutic agent comprising an antibody according to any one of [1.]–[6.], [11.] or [12.] or an antibody fragment derived therefrom as effective ingredients.

[35.] A method for therapeutically treating autoimmune diseases, characterized in administering an antibody according to anyone of [1.]–[6.], [11.] or [12.] or an antibody fragment derived therefrom to a patient with autoimmune diseases.

[36.] A method for therapeutically treating rheumatism, characterized in administering an antibody according to any one of [1.]–[6.], [11.] or [12.] or an antibody fragment derived therefrom to a patient with rheumatism.

[37.] A method for therapeutically treating rheumatoid arthritis, characterized in administering an antibody according to any one of [1.]–[6.], [11.] or [12.] or an antibody fragment derived therefrom to a patient with rheumatoid arthritis.

[38.] A method for therapeutically treating osteoarthritis, characterized in administering an antibody according to any one of [1.]–[6.], [11.] or [12.] or an antibody fragment derived therefrom to a patient with osteoarthritis.

[39.] Use of an antibody according to any one of [1.]–[6.], [11.] or [12.] or an antibody fragment derived therefrom for the manufacture of a medicament for treating autoimmune diseases.

[40.] Use of an antibody according to any one of [1.]–[6.], [11.] or [12.] or an antibody fragment derived therefrom for the manufacture of a medicament for treating rheumatism.

[41.] Use of an antibody according to any one of [1.]–[6.], [11.] or [12.] or an antibody fragment derived therefrom for the manufacture of a medicament for treating rheumatoid arthritis.

[42.] Use of an antibody according to any one of [1.]–[6.], [11.] or [12.] or an antibody fragment derived therefrom for the manufacture of a medicament for treating osteoarthritis.

[43.] A method for screening a therapeutic agent of autoimmune diseases, characterized in evaluating the level of a test compound to inhibit the binding between the RGD sequence site of osteopontin and integrin and/or the binding between the SVVYGLR (residues 11–17 of SEQ ID NO: 1) sequence site and integrin.

[44.] A method for screening a therapeutic agent of rheumatism, characterized in evaluating the level of a test compound to inhibit the binding between the RGD sequence site of osteopontin and integrin and/or the binding between the SVVYGLR (residues 11–17 of SEQ ID NO: 1) sequence site and integrin.

[45.] A method for screening a therapeutic agent of rheumatoid arthritis, characterized in evaluating the level of a test compound to inhibit the binding between the RGD sequence site of osteopontin and integrin and/or the binding between the SVVYGLR (residues 11–17 of SEQ ID NO: 1) sequence site and integrin.

BRIEF DESCRIPTION OF DRAWINGS

FIG. 2 shows graphs depicting the inhibition of RGD-dependent and RGD-independent cell adhesion between nOPN and α9-transformed SW480 cell by the murine antibody 2K1.

FIG. 7 shows the comparison of VH amino acid sequences between the murine 2K1 antibody and the template human antibody.

FIG. 8 shows the comparison of VL amino acid sequences between the murine 2K1 antibody and the template human antibody (SEQ ID NO: 20 and variants thereof).

FIG. 9 shows the VH amino acid sequence of the humanized 2K1 antibody (SEQ ID NO: 28) and its nucleotide sequence encoding the amino acid sequence (SEQ ID NO: 27).

FIG. 10 shows the VL amino acid sequence of the humanized 2K1 antibody (SEQ ID NO: 30) and its nucleotide sequence encoding the amino acid sequence (SEQ ID NO: 29).

FIG. 11 shows a scheme for designing primers for amplifying the VH nucleotide sequence for the humanized 2K1 antibody (SEQ ID NOS: 31–36).

FIG. 12 shows a scheme for designing a primer for amplifying the VL nucleotide sequence of the humanized 2K1 antibody (SEQ ID NOS: 39–44).

BEST MODE FOR CARRYING OUT THE INVENTION

Figure 1:
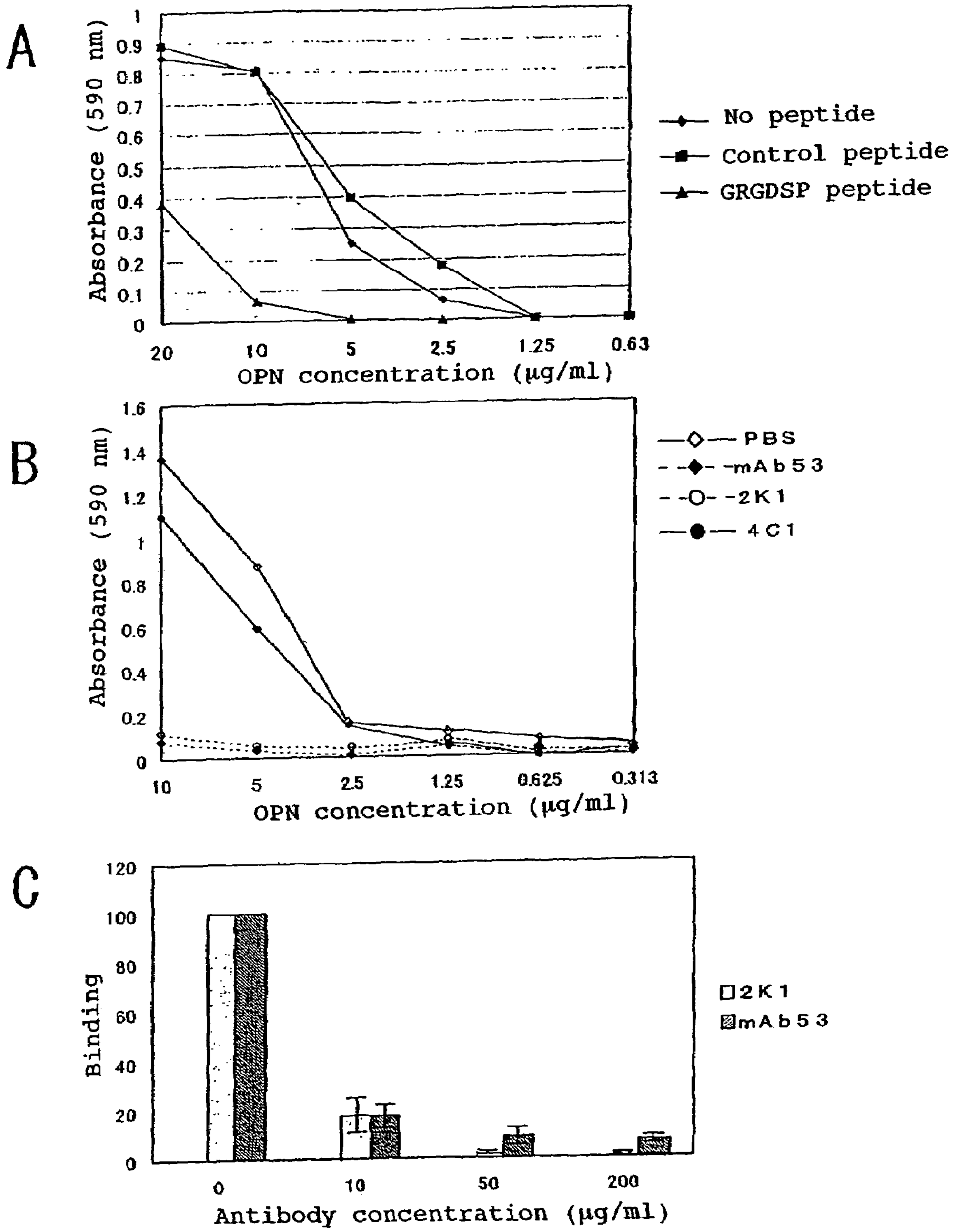
FIG. 1 shows graphs depicting the inhibition of RGD-dependent cell adhesion to OPN.

The chimera anti-osteopontin antibody and the humanized anti-osteopontin antibody in accordance with the invention can be obtained by modifying the constant region of the murine anti-osteopontin antibody (referred to as "OPN inhibitory antibody" hereinbelow) inhibiting the binding between an integrin recognizing the RGD sequence site and OPN or a fragment thereof and also inhibiting the binding between an integrin recognizing the SVVYGLR (residues 11–17 of SEQ ID NO: 1) sequence site or a corresponding sequence site and OPN or a fragment thereof as disclosed in for example the International Application (PCT/JP02/03382) into a chimera antibody (see European Patent Publication EP 0 125 023) or into a humanized antibody (see European Patent Publication EP 0 239 400 or EP 045 126) in a genetically engineering manner so that the resulting antibody can have the same constant region of the antibody in a human or an animal as a therapeutic subject.

Individual classes of antibody molecule have a common fundamental structure, which is composed of a heavy chain of a molecular weight of 50,000–70,000 daltons and a light chain of a molecular weight of 20,000–30,000 daltons. The heavy chain is a polypeptide chain generally containing about 440 amino acid residues. Each class has its own characteristic structure, which is distinctly referred to as γ, ν, α, δ or ε chain corresponding to IgG, IgM, IgA, IgD or IgE, respectively. Further, IgG is classified as IgG1, IgG2, IgG3 or IgG4, each of which is distinctly referred to as γ1, γ2, γ3 or γ4, respectively. As for the light chain two types of L-type and K-type are known, each of which is composed of a polypeptide chain containing about 220 amino acid residues, and is distinctly referred to as λ chain and κ chain, respectively. The peptide composition of the fundamental structure of antibody molecule consists of two equivalent heavy chains and two equivalent light chains that are conjugated together via disulfide bond (S—S bond) and non-covalent bond to form the antibody with molecular weight of 150,000 to 190,000 daltons. Each of the two types of light chains can make pairs with any type of the heavy chain. Each antibody molecule is constantly composed of the same type of two light chains and the same type of two heavy chains.

The heavy chain has four S—S bonds combining intramolecularly (five S—S bonds in the case of the μ or the ε chain), while the light chain has two S—S bonds combining intramolecularly. Each region of 100 to 110 amino acid residues forms one loop. Each the loop resembles each other in its steric structure, and is referred to a structure unit or a domain. The amino acid sequences of N-terminal domains in both the heavy chain and the light chain are not constant, even if the domains are derived from the same class (subclass) of the same animal species. Therefore, the N-terminal domains are called variable region (V region, variable region) (the individual domains are called $V_H$ and $V_L$). The amino acid sequence on the C-terminal side from the domains in each of the classes or in each of the subclasses is almost constant. Therefore, the region is called constant region (C region, constant region) (the individual domains are individually called $C_H1$, $C_H2$, $C_H3$ or $C_L$).

The antigen determining site (epitope) of an antibody is composed of VH and VL. The binding specificity is determined by the amino acid sequence of this site. Meanwhile, the biological activities including the binding with complements and various cells reflect the structural difference in the C region of each Ig class. It has been known that the variability of the variable region in the light and heavy chains is almost limited to three small hyper-variable regions existing in both the chains. These regions are called complementarity determining region (CDR). The remaining part in the variable region is called framework region (FR) and is relatively constant. Generally, only 5 to 10 amino acid residues in the complementarity determining region in each variable region form the antigen determining site.

A protein composed of a mouse-type variable region capable of recognizing an antigen and human-type other remaining regions is called chimera antibody. Further, herein, a chimera antibody recognizing osteopontin and a fragment thereof is called a chimera anti-osteopontin antibody. Still further, a genetically manipulated recombinant protein, which is composed of the complementarity determining region (antigen determining site) derived from an antigen-specific murine monoclonal antibody and all the other remaining regions replaced with those from a human immunoglobulin molecule, is called a humanized antibody. Additionally, herein, a humanized antibody recognizing osteopontin and a fragment thereof is called a humanized anti-osteopontin antibody.

In accordance with the invention, a chimera anti-osteopontin antibody and a humanized anti-osteopontin antibody could be satisfactorily constructed by utilizing any of the OPN-inhibiting antibodies, which can inhibit the binding between the RGD sequence-recognizable integrin such as αvβ1, αvβ3, and αvβ5 and the osteopontin isoform such as OPN-a, OPN-b, OPN-c or an N-terminal fragment thereof and can also inhibit the binding between the SVVYGLR (residues 11–17 of SEQ ID NO: 1) sequence-recognizable integrin such as α9β1, α4β1 and α4β7 and the osteopontin isoform such as OPN-a, OPN-b, OPN-c or an N-terminal fragment thereof. "The sequence SVVYGLR (residues 11–17 of SEQ ID NO: 1) or a corresponding sequence thereof" means those described below: the sequence SVVYGLR (residues 11–17 of SEQ ID NO: 1) means the sequence from serine at position 162 to arginine at position 168 in human OPN, while "the corresponding sequence thereof" means the SVVYGLR (residues 11–17 of SEQ ID NO: 1)-corresponding sequence in the OPN derived from one of other mammals, which is, for example, SVVYGLR (residues 11–17 of SEQ ID NO: 1) from swine identical to the sequence from humans, SVAYGLR (SEQ ID NO: 51) from monkey, SLAYGLR (SEQ ID NO: 52) from mouse and rat, SVAYGLK (SEQ ID NO: 53) from bovine, and SVAYRLK (SEQ ID NO: 54) from rabbit.

The OPN inhibitory antibody of the invention may be prepared by any method, as far as the resulting antibody retains such properties. The OPN inhibitory antibody can be prepared by using as its antigen any one of, for example, OPN-a, OPN-b, OPN-c, or an N-terminal fragment thereof, or by using a peptide containing the amino acid sequence RGDSVVYGLR (residues 8–17 of SEQ ID NO: 1) or a corresponding sequence thereof (referred to as "OPN-related peptide" hereinbelow). The OPN fragment herein referred to means the OPN fragments generated by proteolysis of OPN with proteinases and the like, and includes, for example, a fragment recovered by thrombin proteolysis.

The OPN-inhibitory antibody is preferably prepared by using a peptide containing the sequence RGDSVVYGLR (residues 8–17 of SEQ ID NO: 1) as an antigen. More preferably, the OPN-inhibitory antibody is prepared for example by using as an antigen the peptide (VDTYDGRGDSVVYGLRS) (residues 2–18 of SEQ ID NO: 1) containing both the two sequences in series, which starts from valine residue at position 153 and ends at serine residue at position 169 in OPN-a, and subsequently treating the peptide according to a general method. In order to increase the antigenicity, preferably, a product of the OPN-related peptide bound to a biopolymer compound is used as an antigen.

For research works of OPN-related diseases, using mouse as an experimental animal, preferably, an OPN-inhibitory antibody against murine OPN is used. Such antibody is preferably prepared by using a peptide containing the sequence RGDSLAYGLR (residues 8–17 of SEQ ID NO: 1) as the antigen.

Examples of the biopolymer compound to be bound to the OPN-related peptide include Macroschisma hemocyanin (referred to as "KLH" hereinafter), ovalbumin (referred to as "OVA" hereinafter), bovine serum albumin (referred to as "BSA" hereinafter), rabbit serum albumin (referred to as "RSA" hereinafter), and thyroglobulin. Among them, either KLH or thyroglobulin is more preferable.

The OPN-related peptide and the biopolymer compound can be bound together by known methods, for example the mix acid anhydride process (B. F. Erlanger et al., (1954): J. Biol. Chem. 234, 1090–1094) or the activated ester process (A. E. Karu et al., (1994): J. Agric. Food Chem. 42, 301–309).

The mix acid anhydride for use in the mix acid anhydride process can be recovered by subjecting the OPN-related peptide to general Schotten-Baumann reaction, which is then allowed to react with a biopolymer compound to prepare the object product of the peptide-polymer bound compound. The haloformate ester for use in the mix acid anhydride process includes for example methyl chloroformate, methyl bromoformate, ethyl chloroformate, ethyl bromoformate, isobutyl chloroformate and the like. The ratio of the peptide, the haloformate ester and the polymer compound to be used according to the method is appropriately selected in a wide range.

Herein, the Schotten-Baumann reaction is carried out in the presence of a basic compound. The basic compound for use in the reaction includes compounds for routine use for Schotten-Baumann reaction, for example organic bases such as triethylamine, trimethylamine, pyridine, dimethylaniline, N-methylmorpholine, diazabicyclononene (DBN), diazabicycloundecene (DBU), diazabicyclooctane (DABCO) and the like, and inorganic bases such as potassium carbonate, sodium carbonate, potassium hydrogen carbonate, sodium hydrogen carbonate and the like.

Additionally, the reaction is generally progressed at −20° C. to 100° C., preferably 0° C. to 50° C. The reaction time is about 5 minutes to 10 hours, preferably 5 minutes to 2 hours.

The reaction between the resulting mix acid anhydride and the biopolymer compound is generally practiced at −20° C. to 150° C., preferably 0° C. to 100° C., for a reaction time of about 5 minutes to 10 hours, preferably 5 minutes to 5 hours. The mix acid anhydride method is generally carried out in a solvent. The solvent includes for example any of solvents commonly used for the mix acid anhydride method, specifically including halogenated hydrocarbons such as dichloromethane, chloroform, and dichloroethane; aromatic hydrocarbons such as benzene, toluene and xylene; ethers such as diethyl ether, dioxane, tetrahydrofuran, and dimethoxyethane; esters such as methyl acetate and ethyl acetate; non-protonic polar solvents such as N,N-dimethylformamide, dimethylsulfoxide, and hexamethylphosphotriamide; and the like.

Alternatively, the activated ester process is generally done as follows. Dissolving first the OPN-related peptide in an organic solvent, for reaction with N-hydroxysuccinimide in the presence of a coupling agent, an N-hydroxysuccinimide-activated ester is produced.

As the coupling agent, general coupling agents for routine use in condensation reaction can be used, including for example dicyclohexylcarbodiimide, carbonyldiimidazole and water-soluble carbodiimide. As the organic solvent, alternatively, for example, N,N-dimethylformamide (DMF), dimethylsulfoxide and dioxane can be used. The molar ratio of the peptide and a coupling agent such as N-hydroxysuccinimide for use in the reaction is preferably 1:10 to 10:1, most preferably 1:1. The reaction temperature is 0° C. to 50° C., preferably 22° C. to 27° C., while the reaction time is 5 minutes to 24 hours, preferably one hour to 2 hours. Satisfactorily, the reaction temperature is a temperature of the individual melting points or more to the individual boiling points or less.

After the coupling reaction, the reaction solution is added to a solution dissolving a biopolymer compound therein, for reaction. In the case that the biopolymer compound has a free amino group, for example, an acid-amide bond is formed between the amino group and the carboxyl group of the peptide. The reaction temperature is 0° C. to 60° C., preferably 5° C. to 40° C., and more preferably 22° C. to 27° C., while the reaction time is 5 minutes to 24 hours, preferably one hour to 16 hours, and more preferably one hour to 2 hours.

The reaction product between the OPN-related peptide and the biopolymer compound as generated by the method is purified by dialysis or on a desalting column and the like, to recover the product of the OPN-related peptide bound to the biopolymer compound (simply referred to as "bound product" hereinafter).

Description now follows hereinbelow about the method for preparing an antibody, using the bound product thus recovered as an antigen, and an immunoassay method using the antibody. For the preparation of the antibody, herein, known methods can be utilized, appropriately, which are described in for example Zoku Seikagaku Jikken Koza (Biochemical Experimental Lecture Series), and Men-eki Seikagaku Kenkyu Ho (Immuno-Biochemistry Research Method) (Nihon Seikagaku Gakkai hen (Japan Biochemical Association, ed.)).

In order to prepare a polyclonal antibody using the bound product in accordance with the invention, an animal is immunized with the bound product to collect the antibody from the animal.

More specifically, for example, a bound product such as the OPN-related peptide-thyroglobulin bound product is first dissolved in sodium phosphate buffer (referred to as "PBS" hereinafter), which is then mixed with the Freund complete adjuvant or the Freund incomplete adjuvant, or an auxiliary agent such as alum. The resulting mixture is used as the immunogen for immunization of a mammalian animal.

Any animal for routine use in the field can be used as the animal for immunization, including for example mouse, rat, rabbit, goat and horse. Additionally, the method for dosing the immunogen for immunization may be via any of subcutaneous injection, intraperitoneal injection, intravenous injection, and intramuscular injection. Subcutaneous injection or intraperitoneal injection is preferable. Immunization can be done once or plural times at an appropriate interval, preferably at an interval of one week to 5 weeks. According to a general method, then, blood is collected from the immunized animal, from which serum is separated. By purifying the polyclonal antibody fraction, the OPN inhibitory antibody can be recovered.

According to a general method, additionally, an immune cell recovered by immunizing an animal with the bound product is fused with myeloma cell to prepare a hybridoma. By collecting an antibody from a culture of the hybridoma, the OPN inhibitory antibody can be recovered as a monoclonal antibody.

The chimera anti-osteopontin antibody and the humanized anti-osteopontin antibody in accordance with the invention can be prepared on the basis of the monoclonal OPN-inhibitory antibody or the antibody-generating hybridoma with reference to European Patent Publication EP 0 125 023, EP 0 239 400 and EP 045 126 and the like, as described above. In accordance with the invention, particularly preferably, the chimera antibody or the humanized antibody is prepared from the murine antibody according to the method described in the International Publication WO 94/20632.

In the case that the subject to be treated is human and the OPN inhibitory antibody-generating animal is mouse, preferably, for example, an antibody where the variable region of a murine antibody is conjugated to the constant region of a human antibody (referred to as "chimera antibody" or "chimeric antibody" hereinafter) and an antibody prepared by transplanting mainly the complementarity determining region in the variable region of a murine antibody into a human antibody (referred to as "humanized antibody" hereinafter) are preferably used. For antibody generation, further, a method using a transgenic animal such as mouse introduced with a chimera antibody gene or a humanized antibody gene or the phage display method may satisfactorily be used.

The OPN inhibitory antibody thus recovered can be used as it is. Additionally, the OPN inhibitory antibody may satisfactorily be used in the form of a protein having at least a part of the polypeptides of the heavy chain and/or light chain composing the antibody and being composed of a polypeptide chain with a binding activity to the antigen. Still additionally, the OPN inhibitory antibody may also be used in the form of antibody fragments derived from the OPN inhibitory antibody, such as single-stranded antibody (scFv), Fab and $F(ab')_2$.

So as to prepare the chimera antibody from the murine antibody, specifically, the gene of the variable region of the murine antibody is first cloned with the antibody-generating hybridoma (for example, the hybridoma described in Example 2 (FERM BP-7883)) according to a general method, to determine the nucleotide sequence and the amino acid sequence encoded thereby. The gene of the variable region of the murine antibody as determined in such manner and the leader sequence of the antibody and the like are conjugated to the gene of the constant region of an appropriate class of the human antibody, preferably the gene of the constant region of the IgG class of the antibody, to prepare the chimera antibody gene.

Then, the gene of the chimera antibody is inserted into an appropriate expression vector and is then introduced into cultured cells. Finally, the cells are cultured to obtain the chimera antibody from the culture supernatant.

The thus determined variable region in the murine antibody gene is amplified by PCR using primers having the nucleotide sequences corresponding to the leader sequence and J region of the murine antibody, and is obtained as fragments carrying the variable region of the gene. Preferably, restriction enzyme recognition sites for cloning are introduced to both the ends of these fragments carrying the variable region of the gene.

The gene fragment thus prepared is ligated with the gene fragment carrying the constant region of the human antibody, and the gene for the chimera antibody (simply referred to as "chimera antibody gene" hereinafter) is constructed. The combination is not limited to any specific combination and includes any combination capable of finally expressing the binding activity with the antigen, satisfactorily. Depending on the object, any subclass constant region (for example, a constant region of γ1, γ2, γ3 or γ4 as the heavy chain and the λ or κ chain as the light chain) may be selected. A combination with a constant region gene designed for the enhancement or reduction of the function of the constant region may be satisfactory.

As the expression vector conjugated to the chimera antibody gene thus recovered, expression vectors such as AG-γ1 and AG-κ described in the International Publication WO 94/20632 can be used. However, any vector capable of expressing the chimera antibody gene may be satisfactory, with no specific limitation. Utilization of Ig gene-carrying expression vector AG-γ1 or AG-κ is preferable, because only the insertion of the fragment for variable region derived from murine antibody gene is required to construct an expression vector carrying the chimera antibody gene.

The expression vector can be introduced into culture cells, for example, by the calcium phosphate method.

As for culture cells for introducing the expression vector therein, culture cells such as CHO-DG44 cells can be used and cultured according to general methods.

After being cultured, the chimera antibody accumulated in the culture broth can be purified by various types of chromatography using, for example, protein A column.

The antigenicity of the chimera antibody thus recovered can be assayed by ELISA or BIAcore (BIAcore K.K.) using, for example, osteopontin peptide.

In accordance with the invention, additionally, a humanized antibody closer to the human antibody than the chimera antibody can be prepared, for example, by the method described below.

So as to prepare a humanized antibody from the murine antibody, specifically, the amino acid residues in the complementarity determining region (CDR) in the variable region of the murine antibody are first determined according to the classification of Kabat, et al. (Immunological Interest $4^{th}$ ed., Public Health Service, NIH, Washington D.C., 1987). Amino acid residues mainly around the CDR in the variable region of the murine antibody are transplanted into a template human antibody, to design an amino acid sequence with the CDR of the murine antibody and the framework of the human antibody for the variable region. A nucleotide sequence of DNA encoding the amino acid sequence of the variable region is designed, to prepare a variable gene fragment with the nucleic acid sequence as designed by PCR and genetic recombinant technology. Then, this variable region gene is conjugated to the constant region gene of an appropriate class of the human antibody, preferably the constant region gene of an IgG class antibody, to prepare a humanized antibody gene. Then, the humanized antibody gene is conjugated to an appropriate expression vector, for introduction into a culture cell. Finally, the culture cell is cultured, so that the humanized antibody can be prepared from the culture supernatant.

In the preparation method of the humanized antibody described above, the gene of the complementarity determining region in the variable region gene in the murine antibody can be determined on the basis of the variable region gene of the murine antibody as identified during the preparation of the chimera antibody and within the range of the complementarity determining region according to the Kabat's classification.

As the framework region gene of the template human antibody, alternatively, a sequence highly homologous to the amino acid sequence in the framework region of the murine antibody is selected from for example human germline antibodies. Then, a nucleotide sequence encoding the amino acid sequence is prepared by a general method, which is then satisfactorily used.

Conjugating the complementarity determining region gene of the murine antibody to the framework region gene of the template human antibody, a gene fragment is prepared in the same manner as for the preparation of the chimera antibody. Conjugating the gene fragment to the constant region gene of the human antibody, the gene of the humanized antibody (simply referred to as "humanized antibody gene" hereinafter) is prepared.

Following the preparation of the humanized antibody gene, the introduction of the humanized antibody gene into an expression vector, the introduction of the expression vector into a culture cell, the culturing of the culture cell, the purification of the resulting antibody and the like are then carried out in the same manner as for the preparation of the chimera antibody.

In case of a humanized antibody where only the amino acids in the complementarity determining region are substituted, generally, the antigen-binding activity thereof is frequently reduced than that of the original murine antibody. Therefore, some of the amino acids in the original murine antibody are frequently transplanted, together with some of the amino acids around the complementarity determining region. For the increase of the binding activity and the enhancement of the affinity, further, amino acids not only in the human framework region but also in the variable region may be modified (for example by substitution, insertion, deletion of one or plural amino acids). Antibodies thus prepared are also encompassed within the scope of the humanized antibody of the invention.

A humanized antibody can be obtained by preparing a gene expressing the variable region of the template human antibody where the amino acid sequence mainly around the complementarity determining region of the murine antibody is transplanted in the same manner as in the case of the preparation of the chimera antibody.

The chimera antibody and the humanized antibody (referred to as "recombinant OPN inhibitory antibodies" hereinafter) have antigen binding activities at the same level as that of the original murine antibody and have resolved the problems such as the induction of antigenicity or the reduction of half life.

The recombinant OPN inhibitory antibodies thus recovered are further purified, if necessary, which are subsequently formulated into dosage forms according to a general method, for use in the therapeutic treatment of rheumatoid arthritis, rheumatism such as juvenile articular rheumatism and chronic rheumatism, psoriasis arthritis and psoriasis; the suppression of chronic rejections after organ transplantation; and the therapeutic treatment of autoimmune diseases such as systemic autoimmune diseases, erythematodes, uveitis, Behcet disease, multiple myositis, skein proliferative nephritis, and sarcoidosis.

The recombinant OPN inhibitory antibodies of the invention can preferably be used as a therapeutic agent of rheumatism or a therapeutic agent of rheumatoid arthritis. Examples of the dosage forms of these therapeutic agents of rheumatism and the like include parenteral forms such as injections and infusions, which are preferably dosed via intravenous injection and subcutaneous injection (for use as a therapeutic agent of autoimmune diseases, the examples described above should be followed). For the formulation, additionally, pharmaceutically acceptable carriers and additives may be used within a pharmaceutically acceptable range, depending on the dosage form.

The amount of the recombinant OPN inhibitory antibodies to be added for the formulation varies, depending on the symptomatic severity and age of a patient, the dosage form of the formulation to be used or the binding titer of the recombinant OPN inhibitory antibody or the like. For example, an amount of about 0.1 mg/kg to 100 mg/kg is satisfactorily used.

The recombinant OPN inhibitory antibodies as the effective ingredient in the thus recovered therapeutic agent of the invention strongly bind to the sequences RGD and SVVYGLR (residues 11–17 of SEQ ID NO: 1) in recombinant OPN to inhibit the binding between these OPN regions and integrin. Consequently, thus, the OPN inhibitory antibodies can suppress the exacerbation of the symptoms of rheumatism, and rheumatoid arthritis and other autoimmune diseases.

Because the recombinant OPN inhibitory antibodies of the invention specifically bind to the OPN side, not to the integrin side, the antibodies potentially never inhibit other significant functions of integrin. Therefore, it is expected that disadvantageous side effects can be avoided.

Further, the recombinant OPN inhibitory antibodies of the invention can also be used for the screening purpose of a therapeutic agent of autoimmune diseases. As described above, a compound inhibiting the binding between the RGD sequence of OPN and integrin and inhibiting the binding between the SVVYGLR (residues 11–17 of SEQ ID NO: 1) sequence and integrin possibly serves as a therapeutic agent of autoimmune diseases. Thus, the applicability of a substance to be screened (test substance) as a therapeutic agent of autoimmune diseases can be evaluated in a reaction system prepared by adding the test substance and the recombinant OPN inhibitory antibodies in a competitive manner to an assay system in the presence of given amounts of recombinant OPN and integrin, to assay the extent of the inhibition of the binding between the OPN and integrin relative to the amount of the recombinant OPN inhibitory antibody used.

Similarly, a compound inhibiting the binding between the RGD sequence of OPN and integrin and inhibiting the binding between the SVVYGLR (residues 11–17 of SEQ ID NO: 1) sequence and integrin possibly serves as a therapeutic agent of rheumatism and rheumatoid arthritis. When the recombinant OPN inhibitory antibodies are used to compose the same reaction system as described above, therefore, the reaction system can be used for screening for rheumatism and rheumatoid arthritis.

Furthermore, the recombinant OPN inhibitory antibodies of the invention can be utilized as a diagnostic agent of rheumatism. As described above, it is revealed that a high concentration of the N-terminal fragment of thrombin-cleaved OPN is found in the arthrosis of a patient with rheumatoid arthritis in particular. Thus, the assay of OPN or an N-terminal fragment thereof in a sample using the recombinant OPN inhibitory antibodies can serve for the diagnosis of rheumatism. As the method therefor, the following various methods for use as general immunochemical assay methods ["Hybridoma Method and Monoclonal Antibody", issued by R&D Planning KK., pp. 30–53, Mar. 5, 1982] are applicable: radioimmunoassay method (RIA), ELISA (E. Engvall et al., (1980): Methods in Enzymol., 70, 419–439), fluorescent antibody method, plaque method, spot method, aggregation method, Ouchterlony test and the like.

The method can be selected appropriately from various standpoints. In view of sensitivity, simplicity and the like, ELISA is preferable. The method more preferably includes immobilizing the recombinant OPN inhibitory antibodies of the invention on a carrier and labeling an antibody recognizing an OPN site different from that of the recombinant OPN inhibitory antibodies of the invention, to detect OPN or the N-terminal fragment thereof. Thus, such detection method can be used for a diagnostic agent of rheumatoid arthritis.

The labeling substance for use in the antibody labeling includes enzymes such as horseradish peroxidase (referred to as "HRP" hereinafter) and alkali phosphatase (referred to as "AP" hereinafter), fluorescent substances such as fluorescein isocyanate and rhodamine, radioactive substances such as $^{32}P$ and $^{125}I$, chemiluminescent substances, and the like.

The procedure of for example the sandwich method as one of more specific detection methods of the OPN isoforms is described below. Specifically, the procedure includes a first step (a) of immobilizing an antibody against an OPN isoform of the invention on a carrier, a second step (b) of blocking the carrier surface with no immobilized antibody thereon with a material with no relation with the antigen, for example protein. The procedure further includes a step (c) of adding a sample containing various concentrations of the OPN isoform to the resulting mixture, to generate an OPN isoform-antibody complex, a step (d) of subsequently adding a labeled anti-OPN isoform antibody to allow the antibody to bind to the immobilized antigen-antibody complex, and a final step (e) of assaying the amount of the label bound to the carrier to determine the amount of the OPN isoform free in the sample, based on a preliminarily prepared standard curve.

The carrier used at the step (a) for antibody immobilization includes, but is not specifically limited to any carriers for routine use in immunochemical assay methods. The carrier can include for example polystyrene 96-well microtiter plate or microtiter plate of amino group-bound type. For further antibody immobilization, for example, a buffer containing the antibody is satisfactorily added to and incubated with the carrier. Known buffers can be used as the buffer, which is for example 10 mM PBS. The concentration of the antibody in a buffer may be selected within a wide range. Generally, the concentration is appropriately about 0.01 to 100 μg/ml and preferably 0.1 to 20 μg/ml. Additionally, the amount of the buffer is 300 μl/well or less and preferably about 20 to 150 μl/well, when a 96-well microtiter plate is used as a carrier. Further, the incubation conditions include but are not specifically limited to overnight incubation at about 4° C., which is generally appropriate.

At the step (b) of blocking, further, blocking is done for the purpose of preventing non-specific adsorption on a carrier, because a part possibly adsorbable on a carrier despite no relation with the antigen-antibody reaction may potentially exist in OPN in a sample to be added at the following step. As the blocking agent, for example, bovine serum albumin (BSA) and skim milk solution can be used. Otherwise, commercially available blocking agents such as Block-Ace (manufactured by Dainippon Pharmaceutical Co., Ltd.; Code No. UK-25B) may be used. Specifically but not for limitation, blocking is done by adding for example an appropriate volume of Block-Ace to a part with the antigen immobilized thereon, for overnight incubation at about 4° C. and rinsing the resulting part with a buffer. The buffer includes for example but is not specifically limited to a buffer of the composition of 10 mM PBS, pH 7.2, 0.8% (w/v) NaCl, 0.02% (w/v) KCl, and 0.02% (v/v) Tween 20.

At the step (c), then, a sample containing an OPN isoform is put in contact to the immobilized antibody, to allow the OPN isoform to be captured on the immobilized antibody to prepare an immobilized antibody-OPN isoform complex. With no limitation, the reaction is done at about 37° C. for about one hour. After the completion of the reaction, the carrier is rinsed with a buffer, to discard unreactive protein and the like. A buffer of the composition of 10 mM PBS, pH 7.2 and 0.05% (v/v) Tween 20 is preferable as the buffer to be used for the reaction.

At the step (d), further, an immobilized antibody-OPN isoform-labeled antibody complex is formed by adding a labeled antibody recognizing another epitope of the OPN isoform captured on the immobilized antibody. After completion of the reaction, preferably, the carrier is rinsed with a buffer, to discard unreactive protein and the like. The buffer described for the step (c) is used as the buffer for the reaction.

The labeled antibody to be used at the step (d) is required to recognize an epitope differing from the epitope recognized by the immobilized antibody at the step (a). When a polyclonal antibody recognizing the preceding-half domain of the OPN isoform is used as the immobilized antibody, for example, a polyclonal antibody recognizing the latter-half domain of the OPN isoform is used as the labeled antibody bound with an enzyme (for example, HRP or AP or the like). The use of such antibodies recognizing different sites as described above enables highly sensitive, specific assay of an OPN isoform prepared by selective splicing.

The quantity of the labeled antibody to be used at the step (d) is preferably about 5,000 to 10,000-fold the quantity of the immobilized antibody bound to the carrier. Desirably, the labeled antibody diluted preferably to a final peak absorbance value of 1.5 to 2.0 at the final assay is used for reaction. For such dilution, buffers can be used, while the reaction is done preferably at about 37° C. for about 30 minutes, followed by rinsing with buffers after completion of the reaction. But the reaction is not limited to such conditions. The reactions described above enable the binding of the antibody-OPN isoform-labeled antibody complex to the carrier.

At the step (e), finally, a chromogenic substrate solution reacting with the labeling substance in the immobilized antibody-OPN isoform-labeled antibody complex is added for absorbance measurement to calculate the OPN quantity based on a standard curve.

When an enzyme peroxidase is used as the labeling substance to label an antibody, for example, a chromogenic substrate solution containing hydrogen peroxide and 3, 3', 5,5'-tetramethylbenzidine (TMB) or o-phenylenediamine (OPD) can be used. With no specific limitation, chromogenic reaction is done by adding a chromogenic substrate solution for reaction at about 25° C. for about 20 minutes, and subsequently adding 1N sulfuric acid to terminate the enzyme reaction. In the case that TMB is used, the progress of chromogenic reaction is assayed on the basis of the absorbance at 450 nm. In the case that an enzyme AP is used as a labeling substance, alternatively, an appropriate method includes chromogenic reaction using p-nitrophenylphosphoric acid (pNPP) as a substrate, the addition of 2N NaOH to terminate the enzyme reaction and the measurement of the absorbance at 415 nm.

Using a standard curve preliminarily prepared on the basis of the absorbance of a reaction solution with addition of known concentrations of an OPN isoform, the concentration of the OPN isoform in a sample can be calculated.

The method for detecting the OPN isoform in accordance with the invention is used for the elucidation of OPN functions, and the diagnosis and therapeutic treatment of diseases for which OPN is responsible. One example of the use of the method includes a detection kit of inflammatory abnormalities, by which rheumatism and rheumatoid arthritis for example can be discriminated, the kit working for separately detecting the N-terminal fragment of thrombin-cleaved OPN and non-cleavage-type OPN, thereby detecting the presence or absence of any inflammatory abnormalities.

As described above, particularly, the N-terminal fragment of thrombin-cleaved OPN is likely observed at a high concentration in the articular cavities of patients with rheumatoid arthritis. In patients with osteoarthritis, however, the tendency is significantly low. As described above, the ratio of the N-terminal fragment occupying OPN in articular cavity varies in the individual patients. In order to discriminatively diagnose rheumatism and osteoarthritis, therefore, the ratio of the N-terminal fragment occupying the total OPN can be measured, satisfactorily.

As a more specific example, antibodies against individual peptides of the following three sequences common to all three OPN isoforms namely OPN-a, OPN-b and OPN-c should be raised.

CVDTYDGRGDSVVYGLRS
(C + V153 to S169) (1)

KSKKFRRPDIQYPDATDEC
(K170 to E187 + C) (2)

IPVKQADSGSSEEKQC
(I17 to Q31 + C) (3)

Among them, the sequence (1) is present on the N-terminal side of the thrombin-cleaved site, and is present common to the full-length OPN as the thrombin-non-cleavage type and the N-terminal fragment. Alternatively, the sequence (2) is present on the C-terminal side of the thrombin-cleaved site and is present in the full-length OPN of the thrombin-non-cleavage type but is never contained in the N-terminal fragment. Further, the sequence (3) corresponds to the amino acid residues at positions 17 to 31 on the N-terminal side of OPN and is present common to the full-length OPN as the thrombin-non-cleavage type and the N-terminal fragment. The diagnosis kit for discrimination between rheumatism patients and osteoarthritis patients can be composed of two types of immunoassay reagents utilizing antibodies individually corresponding to the three types of sequences of peptides. In other words, a first immunoassay reagent using two types of antibodies against the peptides represented by the sequences (3) and (2) works for the assay of thrombin-non-cleavage type OPN commonly recognized by both the antibodies in a sample. Then, detection can be done by the same method as the sandwich method, which includes immobilizing for example an antibody against the peptide of the sequence (3) on a carrier, allowing the antibody to react with a sample from a patient, rinsing the carrier, and subsequently adding an antibody against the peptide of the sequence (2) as a labeling antibody. In the case of a second immunoassay reagent, additionally, two antibodies against the peptides represented by the sequences (1) and (3) are used to assay a total of the thrombin-non-cleavage-type OPN and the N-terminal fragment generated by thrombin cleavage in a sample, which are commonly recognized by both the antibodies. In that case, detection can be done by the same method as the sandwich method, which includes immobilizing for example an antibody against the peptide of the sequence (1) on a carrier, allowing the antibody to react with a sample from a patient, rinsing the carrier, and subsequently adding an antibody against the peptide of the sequence (3) as a labeling antibody. Subsequently, the assay results of the sample from the same patient with the two types of the immunoassay reagents are compared together, to elucidate the ratio of the thrombin-cleavage-generated N-terminal fragment in the total OPN in the patient, which enables discrimination between rheumatism and osteoarthritis.

EXAMPLES

The invention will now be described in more detail in the following Examples and Reference Example. But the invention is not limited to these Examples. In these Examples, herein, experiments using commercially available kits and reagents were done according to attached protocols, unless otherwise stated.

Example 1

Cloning, Construction, Purification and Reagents for GST-OPN Fusion Protein:

Cloning and protein purification were done essentially according to the method described in the reference (S. Kon et al., (2000): J. Cell. Biochem. 77: 487–498).

The cDNAs of the human OPN isoforms i.e. OPN-a and OPN-b were recovered as follows. Using RNA prepared from NRC-12 cells of a human kidney cancer cell line as template, cDNA was synthetically prepared; using the cDNA as template, PCR was done using the following primers OPN-5 and OPN-3 to recover cDNAs encoding the full-length human OPN-a and OPN-b individually including the respective signal peptide regions.

In the manner as described in the reference, then, the thus cloned cDNAs of OPN-a and OPN-b were inserted in pGEX4T vector (Amersham Pharmacia Biotech, Tokyo, Japan) so that the cDNAs might be in the same reading frame as that of the GST gene (glutathione S-transferase; EC2.5.1.18), for expression in the form of GST fusion protein, using *Escherichia coli* JM109 (the GST-OPN fusion proteins thus recovered are referred to as "GST-OPN-a" and "GST-OPN-b" hereinbelow).

```
OPN-5:
5'-CGGGATCCACTACCATGAGAATTGCAGTGATTTGC-3'

OPN-3:
5'-CCGCTCGAGTTAATTGACCTCAGAAGATGCACTATC-3'
```

The cDNA encoding human OPN-c isoform was prepared by two-step PCR using the OPN-a cDNA as template. At a first step, PCR was individually done using OPN-5 and the following OPNct-3 primer or the following OPNct-5 and OPN-3 primer; the resulting two PCR products were mixed together, thermally treated, and gradually cooled for annealing, followed by addition of an enzyme for extension. At a second step, subsequently, PCR was done using the OPN-5 and OPN-3 primers, to recover cDNA encoding the full-length human OPN-c including the signal peptide region. The cDNA of the isoform c was integrated in pGEX4T vector by the same method as for the isoforms a and b, for preparing a GST fusion protein (referred to as "GST-OPN-c" hereinafter).

```
OPNct-3:
5'-ACACAGCATTCTTTTCCACAGAACTTCCAGAATCAGC-3'

OPNct-5:
5'-TGAGGAAAAGAATGCTGTGTCCTCTGAAGAAAACC-3'
```

The cDNA encoding the half moiety at the amino terminal side (M1-R168) from the thrombin-cleaved site of OPN-a was recovered by PCR using the OPN-a cDNA as template and OPN-5 together with the following OPNnh-3 primer described below. By the same method as for the isoforms a and b, the resulting cDNA was integrated in the pGEX4T vector to prepare a GST protein (referred to as "GST-N half" hereinbelow).

```
OPNnh-3:
5'-GCCTCGAGTTACCTCAGTCCATAAACCACACT-3'
```

The osteopontin protein (hOPN C half) on the carboxyl side from the thrombin-cleaved site of OPN-a was prepared by two-step PCR using the OPN-a cDNA as template. At a first step, PCR was done, individually, using OPN-5, the following OPNch-3 primer, the following OPNch-5 and the OPN-3 primer. At a second step, PCR was done using the OPN-5 and OPN-3 primers, to prepare the OPN protein on the carboxyl side. By the same method as for the isoforms a and b, recombination into pGEX4T vector enabled the preparation of a GST protein (referred to as "GST-C half" hereinafter).

```
OPNch-3:
5'-TCTTAGATTTGGCACAGGTGATGCCTAGGAG-3'

OPNch-5:
5'-CACCTGTGCCAAATCTAAGAAGTTTCGCAGA-3'
```

Various recombinant GST-OPN fusion proteins were prepared in *Escherichia coli* by a general method, and were then purified, using a glutathione-Sepharose column according to the method described in the reference. Among them, the GST-N half protein was cleaved at the binding site with a prescission protease (PreScission; Amersham Pharmacia Biotech, Tokyo, Japan), to eliminate the GST protein moiety and thereby recover a protein (referred to as "nOPN" hereinafter) composed of the amino-terminal half moiety (I17-R168) of OPN alone.

Alternatively, the cDNA encoding the full-length OPN-a (M1-N314) was further inserted in pcDNA3.1 (+) vector (Invitrogen Corporation), for transfection into CHO-K1 cell (manufactured by Dainippon Pharmaceutical Co., Ltd.) (referred to as "CHO/OPN-a cell" hereinafter). The OPN-a of the sugar chain-bound type (referred to as "CHO/OPN-a" hereinafter) as recovered from the cell was purified as follows. Specifically, the culture supernatant of the CHO/OPN-a cell was subjected to ion exchange column chromatography using a DEAE-Sepharose CL-6B column (Amersham Pharmacia Biotech, Tokyo, Japan) and gel filtration chromatography on an ULTROGEL AcA44 column (manufactured by BioSepra SA), and continuously to reverse-phase column chromatography on a RESOURCE RPC column (Amersham Pharmacia Biotech, Tokyo, Japan). In such manner, purification was completed.

Various peptides used for research works on immune sensitization and binding were purchased from Sigma Genosis Japan or such peptides were obtained by chemical synthesis by the Fmoc (N-(9-fluorenyl)methoxycarbonyl) process with a peptide synthesizer (Model 432 A; manufactured by PerkinElmer Life Science, Inc.) and purification by C18 reverse-phase column chromatography.

Example 2

Production of Murine Monoclonal Antibodies:

Synthetic peptides corresponding to the inner sequences of human OPN were prepared, as shown below, which were then used for immunization.

```
Peptide 1:
CVDTYDGRGDSVVYGLRS (C + V153 to S169)

Peptide 2:
CIDSQELSKVSREFHSH (C + I261 to H276)
```

Specifically, the Peptide 1 has the sequences RGD and SVVYGLR (residues 11–17 of SEQ ID NO: 1) recognizing the $\alpha V\beta 3$ and $\alpha 9$ µl integrin receptors, respectively.

These peptides were bound to thyroglobulin, which were then used for murine immunization according to a general method. Continuously, splenocytes were isolated from the immunized mice, which were then subjected to cell fusion with a murine myeloma cell P3-X63-Ag8-653, using polyethylene glycol. According to the method described in the reference (M. Kinebuchi et al., (1991): J. Immunol., 146, 3721–3728), a hybridoma reacting with each of the peptides used for the immunization was selected.

From mice immunized with the peptides 1 and 2 were recovered monoclonal antibodies designated 2K1 and 4C1, respectively. The hybridoma generating the monoclonal antibody 2K1 was deposited as FERM BP-7883 at the Patent Organism Depository Center, the National Institute of Advanced Industrial Science and Technology (AIST Tsukuba Central 6, 1-1-1, Higashi, Tsukuba-shi, Ibaraki 305–8566, Japan) on the date of Jun. 20, 2001. Additionally, the monoclonal antibody 53 (mAb53) was recovered by immunization with the full-length recombinant human OPN (D. S. Bautista et al., (1994): J. Biol. Chem., 269, 23280–23285).

Example 3

Reactivity of OPN and Thrombin Digestion Products Thereof with the Murine Monoclonal Antibodies:

The binding potencies of the murine monoclonal antibodies 2K1 (referred to as "murine 2K1 antibody" hereinafter) and 4C1 recovered in the Example 2 to OPN and the thrombin digestion products thereof were tested by Western blotting method. It was found that the murine antibody 2K1 reacted with GST-OPN-a, GST-OPN-b, GST-OPN-c and GST-N half. It was found that the antibody 4C1 reacted with GST-OPN-a, GST-OPN-b, GST-OPN-c and GST-C half. Further, these monoclonal antibodies were not only bound to the recombinant OPNs of non-glycosylated type as generated in *Escherichia coli* but also reacted with the CHO/OPN-a protein of sugar-chain-bound type and the thrombin digestion products thereof (referred to as "thrombin-cleaved OPN" hereinafter).

Example 4

Inhibition of Cell Adhesion to OPN Via the Murine Monoclonal Antibodies:

It was examined by the following method as to whether or not the murine monoclonal antibodies inhibited cell adhesion to OPN. First, a 96-well plate was precoated with various concentrations of the CHO/OPN-a at 4° C. overnight, which was then treated with 0.5% BSA in PBS under conditions of 37° C. for 10 minutes, so as to block non-specific adhesion. A human fibroblast TIG-7 or SW480 cell transformed with the cDNA of an integrin subunit $\alpha 9$ (referred to as "$\alpha 9$-transformed SW480 cell" hereinafter) was suspended in D-MEM containing 0.25% BSA; 200 µl of the resulting cell suspension (at a cell concentration of $5\times10^4$ cells/well) was injected in a 96-well plate precoated with the CHO/OPN-a or nOPN, in the presence or absence of various concentrations of the monoclonal antibodies or synthetic peptides, for incubation at 37° C. for one hour.

The culture medium was discarded from the plate, and all the wells were rinsed twice with D-MEM containing 0.25% BSA. The adherent cells were fixed and stained with 0.5% crystal violet in 20% methanol for 30 minutes.

All the wells were rinsed three times with water, and the adherent cells were then solubilized into 20% acetic acid. The resulting supernatant recovered from each well was analyzed with an immunoreader, to measure the absorbance at 590 nm to determine the relative count of the cells adhering to the well. All the assays were done in a triplicate fashion, and at least three independent experiments were performed. The values shown represent mean at three independent experiments.

It has been known that TIG-7 highly adheres to OPN, but as shown in FIG. 1A, the adhesion is apparently inhibited by the peptide GRGDSP (SEQ ID NO: 55) (100 µg/ml) but not inhibited by a control peptide (K296–N314 as the C-terminal region of OPN) (100 µg/ml). Thus, the adhesion is dependent on RGD. As shown in FIG. 1B, further, the murine 2K1 antibody at 200 µg/ml apparently inhibited the cell adhesion to OPN. As shown in FIG. 1C, still further, the effect of murine 2K1 on the inhibition of cell adhesion is comparative to the effect exerted by mAb53 and is concentration-dependent. Still further, murine 2K1 and mAb53 never inhibit the adhesion of TIG-7 cell to vitronectin (VN) or fibronectin (FN).

FIG. 2 depicts the inhibition of the monoclonal antibodies on the adhesion of nOPN and vitronectin to the $\alpha 9$-transformed SW480 cell. As shown in FIG. 2A, the adhesion between 1 μg/ml vitronectin and the α9-transformed SW480 cell was inhibited by 200 μM GRGDSP (SEQ ID NO: 55) (RGD) peptide, so the adhesion is dependent on the RGD. The adhesion of the α9-transformed SW480 cell to 3 μg/ml nOPN was inhibited by using a combination of 200 μM GRGDSP (SEQ ID NO: 55) (RGD) peptide and an anti-α9β1 monoclonal antibody Y9A2 (A. Wang et al., (1996): Am. J. Respir. Cell Mol. Biol., 15, 664–672), so the adhesion is RGD-dependent and RGD-independent. FIG. 2B additionally shows the effect of murine 2K1 on the adhesion of the α9-transformed SW480 cell to nOPN and vitronectin. The adhesion between the α9-transformed SW480 cell and vitronectin was never inhibited by the murine 2K1 antibody, but the adhesion between the SW480 cell and nOPN was inhibited by the murine 2K1 antibody. Consequently, it is indicated that the murine 2K1 antibody retains the potency of inhibiting RGD-dependent adhesion.

Example 5

Inhibition of Opn-Induced Monocyte Migration Via the Murine Monoclonal Antibodies:

A cell migration test using the U937 cell was performed by using a system ChemoTx101-8 (Neuro Probe Inc.). The cell was adjusted to $2\times10^6$ cells/ml with D-MEM containing 0.1% BSA, which was then applied to the upper layer on a filter (with a pore size of 8 μm), while the OPN protein was added to the lower layer.

The ChemoTx plate was left to stand in the presence of 5% $CO_2$ at 37° C. for 4 hours. After the plate was left to stand, the filter was fixed with methanol, and was then stained with hematoxylin and eosin (H-E). The number of the cells migrating to the back face of the filter was counted with a microscope (magnification×400). The test was done in a triplicate manner, and the mean was used as data. The results are shown in FIG. 3.

Figure 3A:
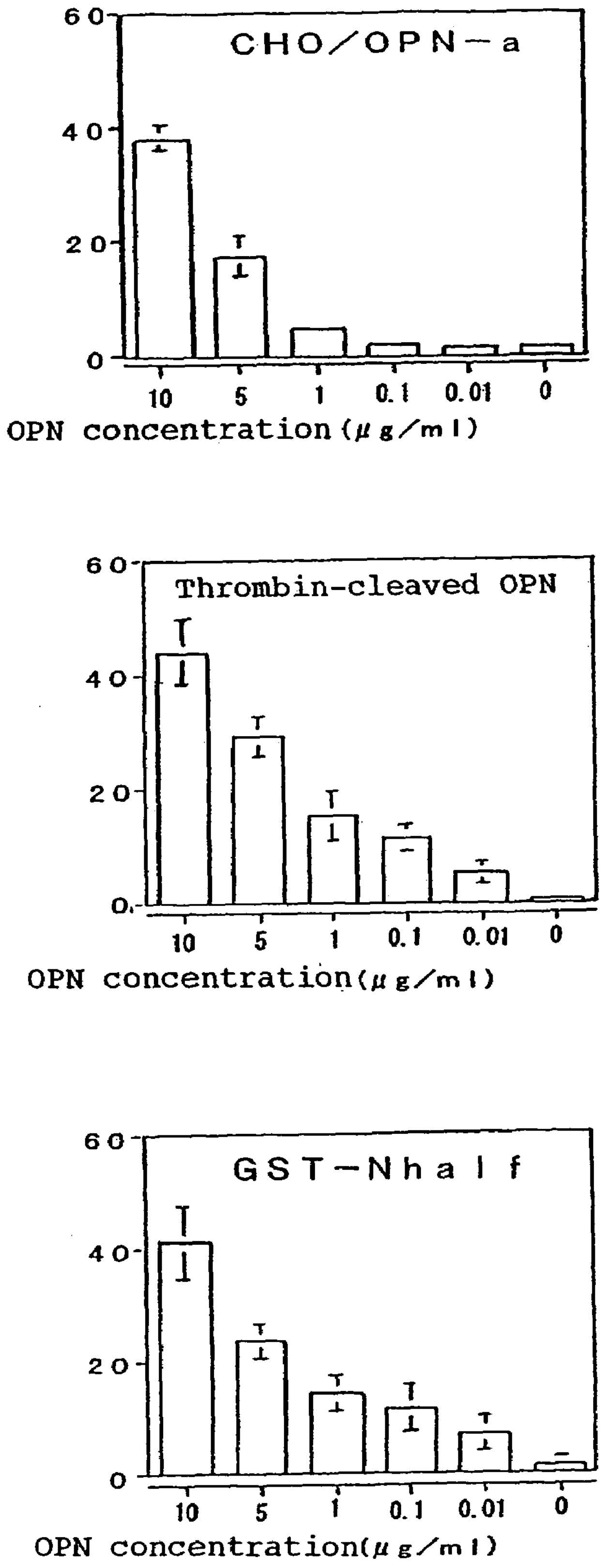
FIG. 3*a* shows graphs depicting OPN-induced cell migration.

FIG. 3*a* shows cell migration of the U937 cell toward the CHO/OPN-a, the thrombin-cleaved OPN and the GST-N half at the concentrations shown. Additionally, FIG. 3*b* shows inhibition assays using the individual OPNs at 10 μg/ml, in the presence or absence of the murine 2K1 antibody, mAb53 or control murine IgG at 50 μg/ml after purification in antigen-specific manners.

Figure 3B:
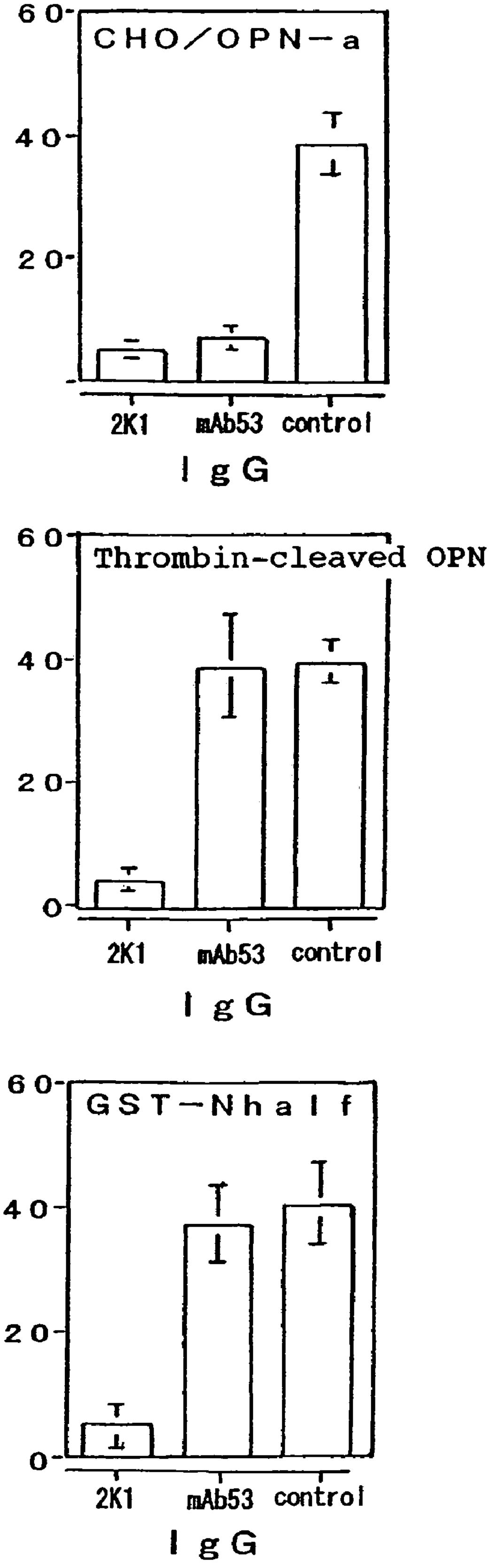
FIG. 3*b* shows graphs depicting the suppression of OPN-induced cell migration by antibodies.

As shown in FIGS. 3*a* and 3*b*, the CHO/OPN-a, the thrombin-cleaved OPN and the GST-N half induce the migration of the human monocyte U937 in a concentration-dependent manner (A). The murine 2K1 antibody apparently inhibits the monocyte migration induced by the CHO/OPN-a, the thrombin-cleaved OPN and the GST-N half. On contrast, mAb53 only inhibits only the monocyte migration induced by the full-length OPN (B).

Reference Example 1

OPN and Arthritis Induction:

In order to elucidate the OPN function in arthritis, an OPN gene-defective mouse (S. R. Rittling et al., (1998): J. Bone and Mminer. Res., 13 (7), 1101–1111) was artificially prepared according to a general method, for comparative experiments with normal mouse.

An arthritogenic monoclonal antibody cocktail commercially available as a substance eliciting arthritis (under the trade name of a cocktail for arthritis, Arthrogen-CIA® mAb, Arthritogenic mAb cocktail; manufactured by Iwai Chemical Pharmaceutical Co., Ltd.) was administered to the OPN gene-defective mouse (OPN $^{-/-}$) and a normal mouse (OPN $^{+/+}$), individually, according to an instruction manual attached to the product, for arthritis induction. Then, the severity thereof was observed. For controls, physiological saline was dosed to the two types of the mice.

Figure 4:
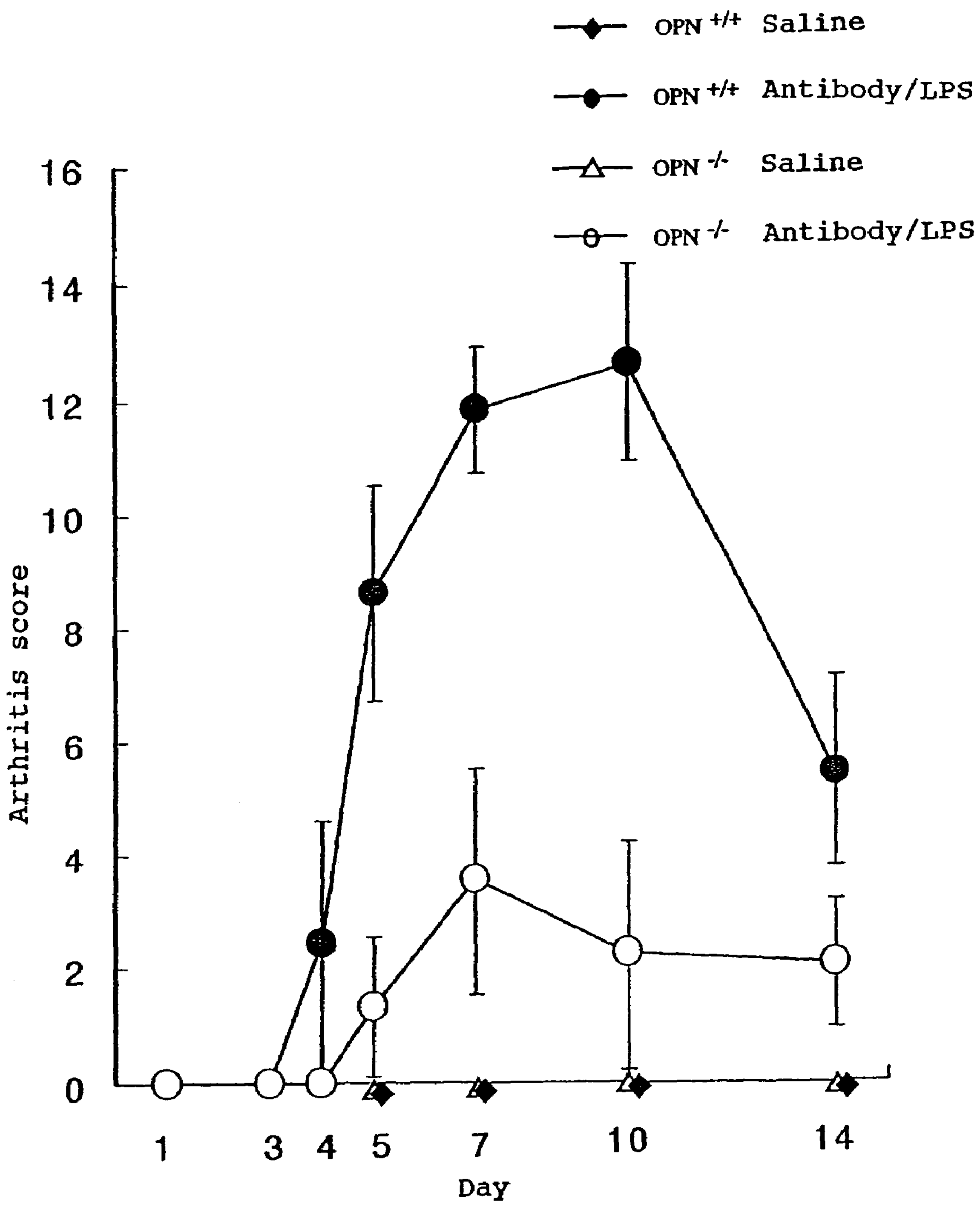
FIG. 4 shows graphs depicting the time course of the change of arthritis score for an OPN gene-defective mouse in comparison with that for a normal mouse when the arthritogenic antibody cocktail/LPS was individually dosed to these mice.

Comparison of the severity of arthritis was made on the basis of arthritis score according to the following standard and wrist swelling on day 10 post-dosing. The results are shown in FIGS. 4 and 5.

As apparently shown in FIG. 4, the normal mouse dosed with the arthritogenic antibody cocktail/lipopolysaccharide (referred to as "LPS" hereinafter) had an increase of the arthritis score on day 4 and thereafter, until on day 10, the score reached maximum (12 or more). Alternatively, the arthritis score of the OPN gene-defective mouse increased on day 5 and thereafter, but the score was only 4 or less at maximum. Additionally, any of the groups dosed with physiological saline had no increase of the arthritis score.

Figure 5:
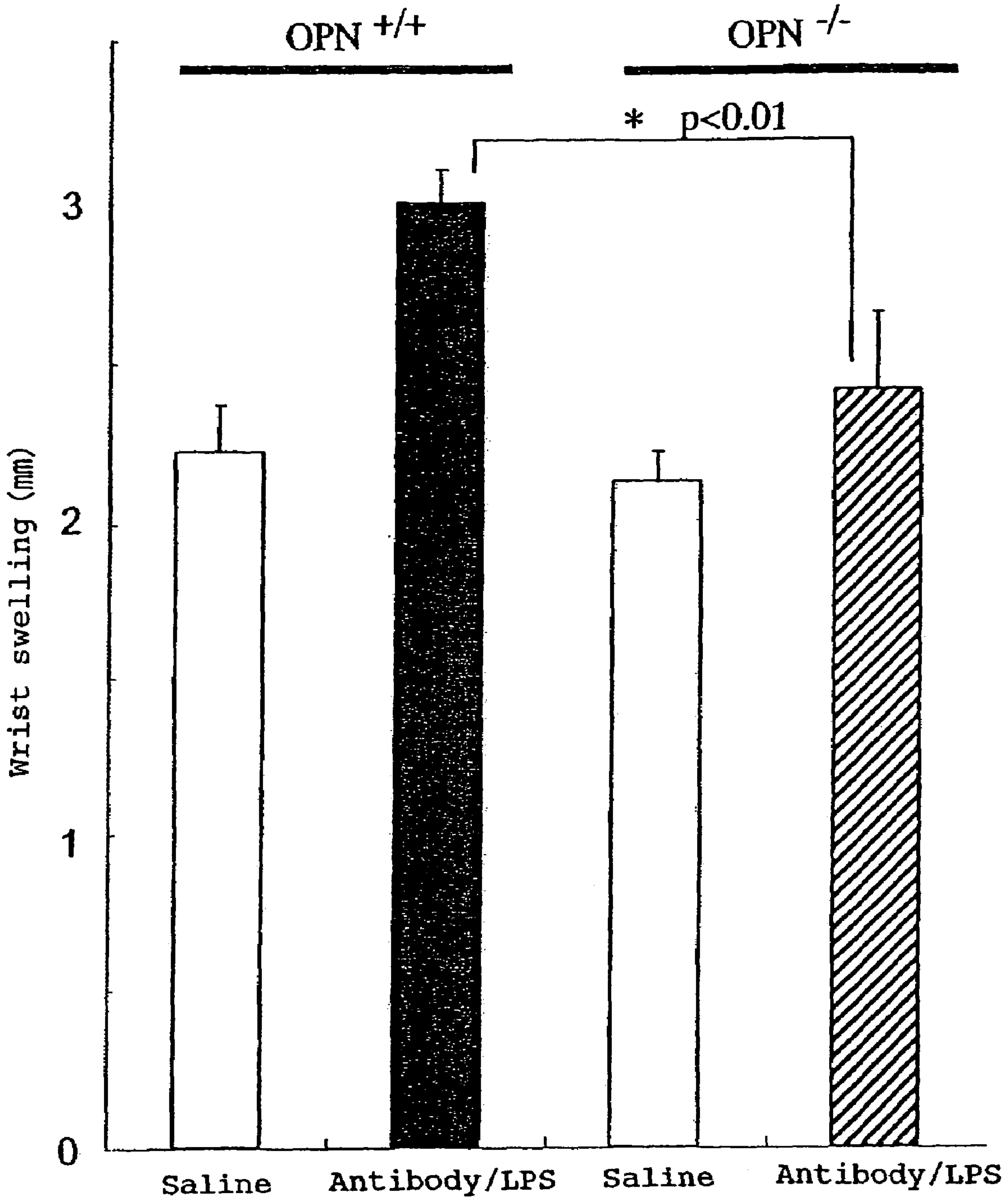
FIG. 5 shows graphs depicting the comparison of wrist swelling in the OPN gene-defective mouse and the normal mouse when the arthritogenic antibody cocktail/LPS was individually dosed to these mice.

As shown in FIG. 5, further, wrist swelling is apparently weak in the OPN gene-defective mouse, compared with the normal mouse, which clearly indicates OPN involvement in arthritis.

Example 6

Inhibitory Activity of Murine 2K1 Antibody on Human Peripheral Leukocyte Migration:

By the following method, the inhibitory activity of the murine 2K1 antibody on cytokine-activated human peripheral leukocyte migration was examined. Table 1 shows the results of the inhibitory activity on neutrophil migration, while Table 2 shows the results of the inhibitory activity on monocyte migration.

<Experimental Method>

By the Ficoll method, a monocyte fraction and a neutrophil fraction were separated from normal human peripheral blood (P. M. Daftarian et al., (1996): Journal of Immunology, 157, 12–20). The intermediate layer between Ficoll and serum was collected and cultured in a flask at 37° C. for one hour. The resulting attached cell was used as monocyte. To the erythrocyte layer remaining after collection of the monocyte fraction was added a 5-fold volume of 3% dextran-PBS to aggregate erythrocyte, followed by centrifugation at 150×g and 4° C. for 5 minutes.

The aggregated erythrocyte was precipitated, while in the resulting supernatant, neutrophil existed in suspended state. Then, the fraction was centrifuged at 500×g and ambient temperature for 20 minutes, to recover neutrophil. The monocyte and neutrophil as recovered in such manner were cultured overnight with human TNF-α (20 ng/mL) for activation. Then, the resulting activated monocyte and neutrophil were used for migration experiments.

The migration experiments were done, using a 48-well micro chemotaxis chamber (manufactured by Neuro Probe Inc.). After various concentrations of the murine 2K1 antibody were added to the thrombin-cleaved OPN and were then preliminarily left to stand at 37° C. for 15 minutes, the mixtures were added to the lower chamber (to a final human OPN concentration of 10 μg/mL). Placing thereon a polycarbonate filter (pore size of 5 μm), further, a cell suspension ($2\times10^6$ cells/mL) of 50 μL was added to the upper chamber.

After culturing in the presence of 5% $CO_2$ at 37° C. for 2 hours, the polycarbonate filter was removed to discard the cells on the upper surface of the filter; subsequently, the cells infiltrating to the back face of the filter were stained with Diff-Quick (manufactured by Baxter International Inc.). The stained cells were counted at a magnification×40. The results are shown as mean cell counts (cells/$mm^3$)±SD in 6 wells.

<Experimental Results>

The murine 2K1 antibody inhibited the migration of the TNF-α-activated human peripheral neutrophil and monocyte toward the thrombin-cleaved OPN.

Inhibition of neutrophil migration:

TABLE 1

| Concentration of thrombin-cleaved OPN (μg/mL) | Murine 2K1 antibody concentration (μg/mL) | Mean migrating cell counts per 1 $mm^3$ |
|---|---|---|
| 0 | 0 | 400.0 ± 67.8** |
| 10 | 0 | 581.7 ± 67.1 |
| 10 | 0.4 | 566.7 ± 60.2 |
| 10 | 2 | 550.0 ± 49.0 |
| 10 | 10 | 450.0 ± 90.8** |
| 10 | 50 | 426.7 ± 30.8** |

**P < 0.01 (one way ANOVA, Dunnett's test)

Inhibition of monocyte migration:

TABLE 2

| Concentration of thrombin-cleaved OPN (μg/mL) | Murine 2K1 antibody concentration (μg/mL) | Mean migrating cell counts per 1 $mm^3$ |
|---|---|---|
| 0 | 0 | 58.3 ± 50.8** |
| 10 | 0 | 285.0 ± 49.3 |
| 10 | 0.4 | 258.0 ± 71.9 |
| 10 | 2 | 256.7 ± 66.5 |
| 10 | 10 | 160.0 ± 56.9** |
| 10 | 50 | 75.0 ± 55.4** |

**P < 0.01 (one way ANOVA, Dunnett's test)

Example 7

Preparation of Chimera 2K1 Antibody-Expressing Plasmid:

According to the method for preparing the chimera antibody of the anti-HIV monoclonal antibody (C25 antibody) as described in the international publication of International Publication WO94/20632, a mouse-human chimera 2K1 antibody (sometimes referred to as "chimera 2K1 antibody" or "C2K1 antibody" hereinbelow) was prepared by conjugating the gene of the heavy chain variable region (VH) of the murine 2K1 antibody to the human Igγ1 gene and conjugating the gene of the light chain variable region (VL) thereof to the human Igκ, recovered in Example 2.

First, mRNA of a hybridoma generating the murine 2K1 antibody was extracted, using the ISOGEN reagent (Nippon Gene). Using the mRNA as template, cDNA was synthetically prepared using $pd(N)_6$ Random Hexamer and Ready-To-Go You-Prime First-Strand Beads (both manufactured by Amersham Biosciences, Co., Ltd.).

Using the cDNA as template and a primer corresponding to the leader sequence of the VH gene of the murine 2K1 antibody and a primer corresponding to the J region of the VH gene as shown below and as designed according to the classification of nucleic acid sequences of V regions and J regions by Kabat et al. (Immunological Interest $4^{th}$ ed., Public Health Service, NIH, Washington D.C., 1987), subsequently, the VH region was amplified with Ex Taq DNA polymerase (TAKARA SHUZO CO., LTD.).

```
Primer for Leader sequence (VH):
5'-TTCGAAGCTTGCCGCCACCATGGAATGGAGCTGGATCTTT-3'

Primer for J region (VH):
5'-GAAGATCTGGATCCACTCACCTGAGGAAACTGTGA-3'
```

The primer for the leader sequence and the primer for the J region individually contain a restriction enzyme HindIII recognition sequence and a restriction enzyme BamHI recognition sequence for cloning.

Concerning the VL gene, meanwhile, a VL gene fragment with a restriction enzyme HindIII recognition site and a restriction enzyme BamHI site on both the termini was obtained, using a primer corresponding to the following leader sequence and a primer corresponding to the J region, in the same manner as in the case of the VH gene.

```
Primer for Leader sequence (VL):
5'-CTTAAGCTTGCCGCCACCATGAAGTTGCCTGTTAGGCTG-3'

Primer for J region (VL):
5'-CTAGATCTGGATCCACTTACGTTTCAGCTCCAGCTT-3'
```

The VH- and VL gene fragments thus obtained were digested with HindIII and BamHI (both from TAKARA SHUZO CO., LTD.), which were then integrated into expression vectors AG-γ1 and AG-κ (International Publication WO94/20632). Specifically, AG-γ1 has the β actin promoter, the gene of the human immunoglobulin constant region γ1 chain and a selective marker neomycin resistant gene (neo). By inserting the VH gene of the murine 2K1 antibody between the HindIII recognition sequence and the BamHI recognition sequence upstream the γ1 gene, a plasmid expressing the heavy chain of the chimera 2K1 antibody can be prepared. Additionally, AG-κ has the β actin promoter, the gene of the human immunoglobulin constant region κ chain and the dihydrofolate reducing enzyme gene (dhfr) as a selective marker. By inserting the VL gene of the murine 2K1 antibody between the HindIII recognition sequence and the BamHI recognition sequence upstream the κ gene, a plasmid expressing the light chain of the chimera 2K1 antibody can be prepared.

These expression plasmids were introduced in *Escherichia coli* strain HB101 according to a general method, which was then cultured at a mass scale. The resulting plasmids were purified, using EndoFree Plasmid Mega Kit (QIAGEN Inc.).

Example 8

Expression of Chimera 2K1 Antibody:

The expression plasmids of the heavy chain and light chain of the chimera 2K1 antibody as purified above in Example 7 were mixed together and used for transfection of the CHO-DG44 cell strain by a routine calcium phosphate method. Selection on a MEM culture medium (Invitrogen) supplemented with 0.5 mg/ml Geneticin (Invitrogen) and nucleotide-free FCS prepared by dialysis (Invitrogen) at 10% gave a transformant cell generating the chimera 2K1 antibody.

The cell was cultured in 500 ml of the MEM culture medium supplemented with 2% dialyzed FCS. The resulting culture supernatant was passed through a protein A column (Amersham Biosciences, Co., Ltd.) and then dialyzed against PBS, to obtain a purified chimera 2K1 antibody. The concentration of the purified chimera 2K1 antibody was determined, using a DC protein assay kit (BIO-RAD). Finally, 1.4 mg of the purified antibody was obtained.

Example 9

Inhibitory Activity of Chimera 2K1 Antibody on Human Peripheral Monocyte Migration:

By the following method, the inhibitory activity of the purified chimera 2K1 antibody obtained in Example 8 on cytokine-activated human peripheral monocyte migration was examined.

First, the blood drawn out from a normal subject with heparin was diluted 2-fold with an RPMI 1640 culture medium. The diluted blood was overlaid on the Ficoll-Paque (Pharmacia), which was then centrifuged at 400×g at ambient temperature for 30 minutes. A white layer observed in the interface between the blood plasma and Ficoll-Paque was recovered and used as a monocyte. The monocyte thus obtained was overnight cultured with human TNF-α (20 ng/mL). The resulting activated monocyte was used for a migration experiment.

The migration experiment was done, using a 48-well microchemotaxis chamber (Neuro Probe Inc.). Human OPN reacted with bovine thrombin (Sigma) at 37° C. for 2 hours, for cleavage. After various concentrations of the 2K1 chimera antibody were added to the resulting human thrombin and left to stand at 37° C. for 15 minutes, the resulting mixture was added to the lower chamber (the final human OPN concentration was 10 μg/mL). Placing a polycarbonate filter (pore size of 5 μm) thereon, 50 μl of a cell suspension ($2\times10^6$ cells/mL) was added to the upper chamber.

After culturing in the presence of 5% $CO_2$ at 37° C. for 2 hours, the polycarbonate filter was removed, while the cells on the surface of the upper filter were removed and stained with Diff-Quick (Baxter). The cells on the surface of the upper filter were counted at a magnification×40. The results are shown as mean cell count (cells/$mm^3$)±SD in 6 wells.

As shown in Table 3, consequently, the chimera 2K1 antibody inhibited the migration of the TNF-α-activated human peripheral neutrophil and monocyte toward the thrombin-cleavage-type OPN.

Inhibitory activity of monocyte migration:

TABLE 3

| Concentration of thrombin-cleaved OPN (μg/mL) | Chimera 2K1 antibody concentration (μ/mL) | Mean migrating cell counts per 1 $mm^3$ |
|---|---|---|
| 0 | 0 | 955.0 ± 73.6** |
| 10 | 0 | 1335.0 ± 106.9 |
| 10 | 12.5 | 1010.0 ± 59.1* |
| 10 | 25 | 1153.3 ± 96.2 |
| 10 | 50 | 895.0 ± 78.0** |
| 10 | 100 | 821.7 ± 50.2** |
| 10 | 250 | 865.0 ± 64.9** |
| 10 | 500 | 830.0 ± 44.1** |

*P < 0.05
**P < 0.01 (one way ANOVA, Dunnett's test)

Example 10

Figure 6A:
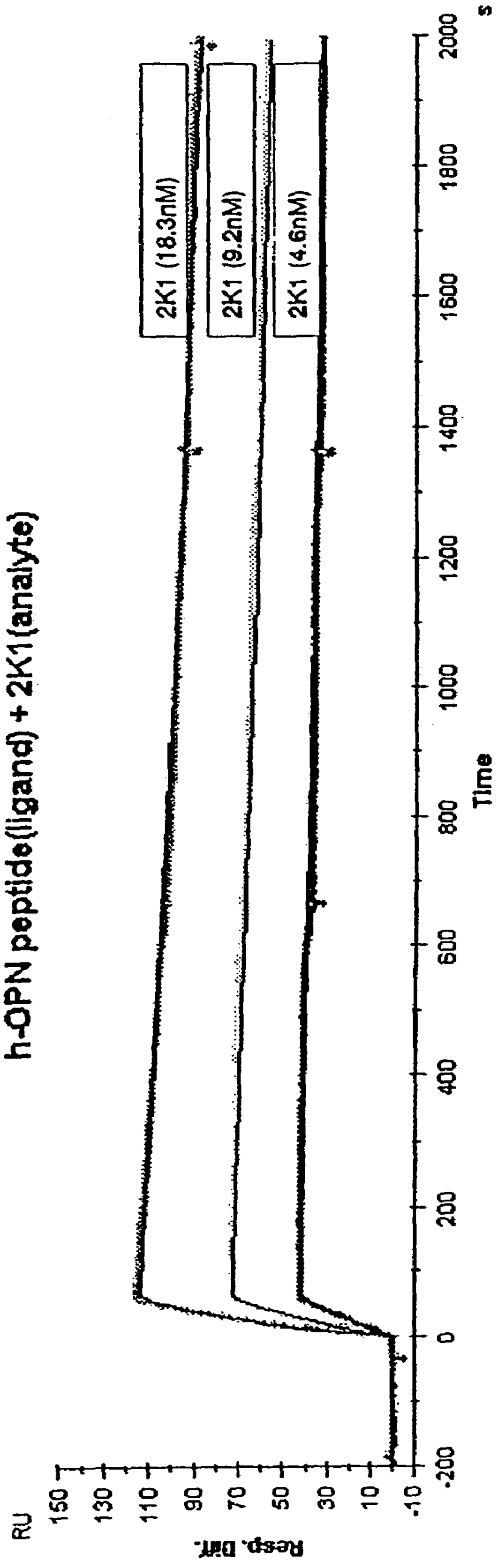
FIG. 6*a* shows a BIACORE-2000 sensor gram using the murine 2K1 antibody as the analyte.
Figure 6B:
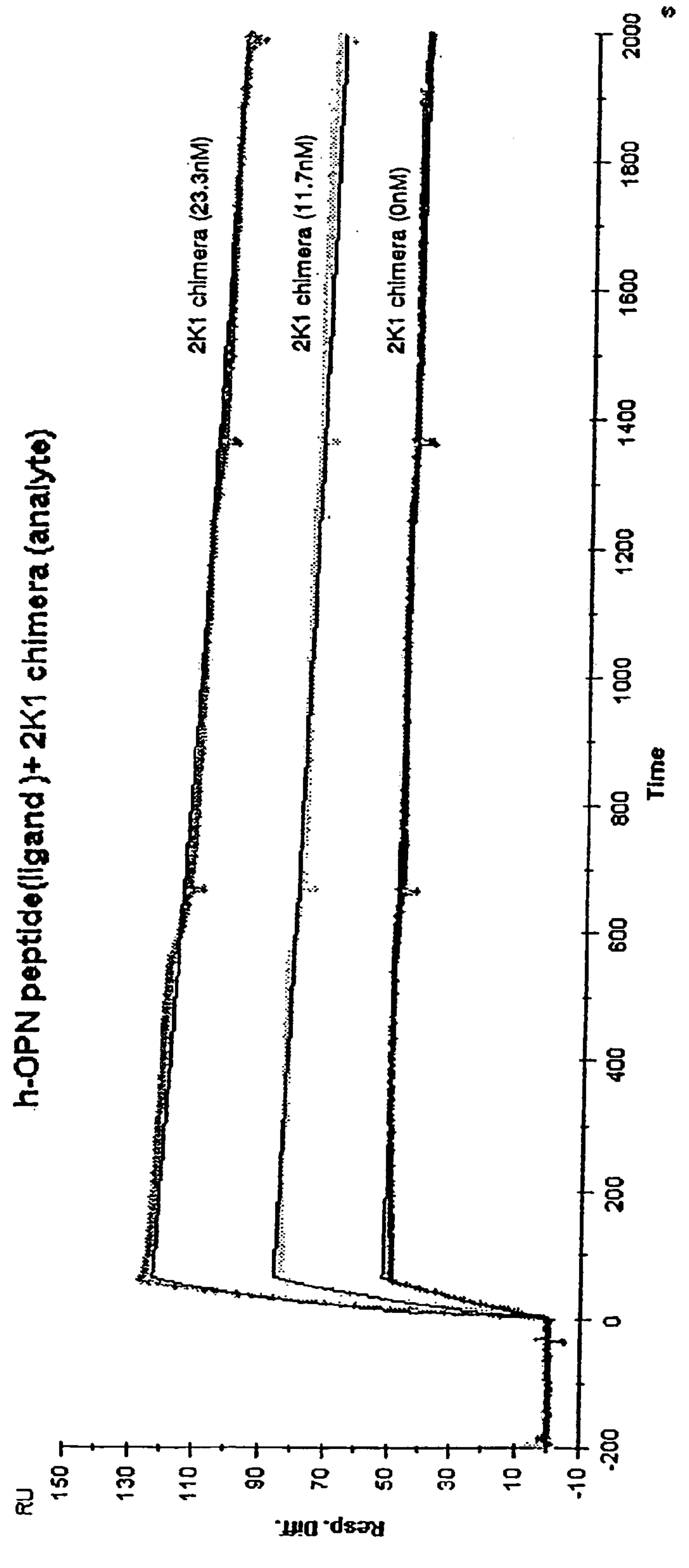
FIG. 6*b* shows a BIACORE-2000 sensor gram using the chimera 2K1 antibody as the analyte.

Assay of KD Value of Chimera 2K1 Antibody:

The KD value of the chimera 2K1 antibody was assayed in the following manner. First, a partial peptide GRGDSVVYGLR (residues 7–17 of SEQ ID NO: 1) of the human osteopontin was biotinylated with a biotinylation kit (Dojindo Corporate). A sensor chip SA was set on BIACORE-2000, to bind 23 RU of a ligand (Bin-GRGDSVVYGLR)(residues 7–17 of SEQ ID NO: 1). Continuously, the murine 2K1 antibody was passed as an analyte, to obtain the sensor gram shown in FIG. 6*a*. Additionally, the chimera 2K1 antibody was passed as an analyte to obtain the sensor gram shown in FIG. 6*b*. In each of the figures, herein, the axis of abscissa shows time, while the axis of ordinate shows relative response (RU). The data of these sensor grams were analyzed by global fitting at 1:1 (Langmuir) binding by a BIACORE analysis software BIA Evaluation Version 3.0. The results are shown in FIG. 6. FIG. 6*a* is a sensor gram at various concentrations of the murine 2K1 antibody. FIG. 6*b* is a sensor gram at various concentrations of the chimera 2K1 antibody.

As the results of the measurement, the KD value of the murine 2K1 antibody was $1.2\times10^{-10}$ M, while the KD value of the chimera 2K1 antibody was $9.2\times10^{-11}$ M. No reduction of the affinity of the chimera 2K1 antibody was observed due to the chimera preparation of the murine 2K1 antibody.

Example 11

Preparation of Humanized 2K1 Antibody Gene:

The template human antibody into which amino acids in the complementarity determining region (CDR) in the VH or VL of the murine 2K1 antibody were to be transplanted was selected from human germline antibodies with amino acid sequences highly homologous to the amino acid sequences of the frameworks (FRs) of the VH and VL of the murine 2K1 antibody. Specifically, a combination of DP-88 (Accession No. Z49804) with JH6 (Accession No. X69866) was selected as the template human VH, while as the template human VL, a combination of DPK-13 (Accession No. X93631) with Jκ2 (Accession No. AJ399904) and a combination of DPK-18 (Accession No. X93635) with Jκ2 were selected. The VH amino acid sequence (SEQ ID No. 19) and VL amino acid sequence (SEQ ID NO: 20) of the murine 2K1 antibody were compared with these VH and VL amino acid sequences of the template human antibody, which are individually shown in FIGS. 7 and 8. The CDR range was shown according to the description in the Kabat et al.'s Classification.

CDR of the VH had the following amino acid sequence.

```
CDR1 (SQ ID No. 21): DYEMH
CDR2 (SQ ID No. 22): AIHPGRGGTAYNQKFKG
CDR3 (SQ ID No. 23): ITGYFDV
```

CDR of the VL had the following amino acid sequence.

```
CDR1 (SQ ID No. 24): RSSQSIVHSNGNTYLE
CDR2 (SQ ID No. 25): KVSNRFS
CDR3 (SQ ID No. 26): FQGSHVPLT
```

A humanized antibody was prepared by transplanting necessary amino acid sequences of the VH and VL in the murine 2K1 antibody into the VH and VL of the template human antibody. Specifically, a nucleotide sequence of DNA encoding an amino acid sequence prepared by substituting the CDR amino acid sequence with the CDR amino acid sequence of the murine 2K1 antibody was designed. As described in the following item, then, a gene fragment of a nucleic acid sequence as designed was prepared by PCR and genetic recombinant technology. For only FR2 of VL, the DPK13 amino acid sequence more highly homologous to the murine 2K1 antibody was selected. For the remaining FR parts, the amino acid sequence of DPK18 was selected. For only FR4 of VH, the JH6 amino acid sequence was selected. For the remaining FR parts, the amino acid sequence of DPK-88 was selected.

The VH and VL amino acid sequences of the humanized 2K1 antibody (sometimes referred to as "R2K1 antibody" hereinbelow) thus prepared and the nucleotide sequences encoding them are individually shown in FIG. 9 (SEQ ID NOS: 27 and 28) and 10 (SEQ ID NOS: 29 and 30). As the leader sequence of the antibody, herein, the same sequence as used in the humanized anti-HIV monoclonal antibody (RC25 antibody) described in the PCT International Publication WO 94/20632 was used (the underlined parts in FIGS. 9 and 10). Additionally, HindIII- and BamHI recognition sites for cloning were added to both the ends of the nucleotide sequences encoding VH and VL.

So as to obtain DNA fragments with the nucleotide sequences shown in FIGS. 9 and 10, actually, total synthesis using oligo DNA by PCR was done. As shown in FIG. 11, specifically for VH, six oligo DNAs (SEQ ID Nos. 31 to 36) were designed and synthesized so as to cover the full-length VH nucleotide sequence in FIG. 9. Using the DNAs, PCR was done by the following procedures. Using a mixture of 10 pmol each of the six types of oligo DNAs as template and Pyrobest DNA polymerase (TAKARA SHUZO CO., LTD.), a step of 96° C. for 20 seconds, 55° C. for 30 seconds and 72° C. for 3 minutes was repeatedly cycled 10 times. Using 1 μl of the resulting PCR product as template, the oligo DNAs of the underlined sequences in FIG. 11 (SEQ ID NO: 37 and 38) as primers and Pyrobest DNA polymerase, then, a step of 96° C. for 20 seconds and 72° C. for 3 minutes was repeatedly cycled 25 times, to amplify the full-length VH. The resulting DNA fragment was ligated to pCR-Blunt vector using Zero Blunt PCR Cloning Kit (Invitrogen) and introduced in *Escherichia coli*, for cloning. From the resulting *Escherichia coli* clones, the plasmid DNA was prepared using QIAprep Spin Miniprep Kit (QIAGEN). Using the plasmid DNA as template, the M13-M4 primer and M13-RV primer (both of TAKARA SHUZO CO., LTD.), and CEQ DTCS-Quick Start Kit (BECKMAN COULTER) for sequencing reaction, the nucleotide sequence of the cloned DNA was analyzed with CEQ 2000 auto-sequencer (BECKMAN COULTER), to obtain a clone with the nucleotide sequence in FIG. 9 as designed.

For VL, six oligo DNAs (SEQ ID NO: 39 to 44) shown in FIG. 12 were used for 10 cycles of PCR in the same manner as described above. Using the amplified product as template and the oligo DNAs with the underlined sequences in FIG. 12 (SEQ ID NO: 45 and 46) as primer, then, 25 cycles of PCR as described above were carried out. By subsequently carrying out the same procedures as for VH, a clone with the nucleotide sequence in FIG. 10 as designed could be obtained.

Example 12

Preparation of Humanized 2K1 Antibody-Expressing Plasmid:

In the same manner as in the case of preparing the chimera 2K1 antibody-expressing plasmid as described in Example 7, a humanized 2K1 antibody-expressing plasmid was prepared. From the clone with the VH and VL genes of the humanized 2K1 antibody prepared in Example 11, the plasmid DNA was extracted by a general method. The clone was digested with HindIII and BamHI, to obtain VH- and VL DNA fragments, which were integrated in the expression vectors AG-γ1 and AG-κ. The expression plasmids expressing the heavy chain of the humanized 2K1 antibody and the light chain thereof thus prepared were introduced in *Escherichia coli*, for mass-scale culturing. Based on the resulting *Escherichia coli*, a plasmid DNA expressing the heavy chain and the light chain was purified for transfection.

Example 13

Expression of Humanized 2K1 Antibody:

The expression plasmid of the heavy chain of the humanized 2K1 antibody prepared in Example 12 was mixed with the expression plasmid of the light chain thereof, which was then used for transfection of a CHO-DG44 cell stain by the calcium phosphate method. Using the culture supernatant of a 3-day culture of the cell strain in an MEM culture medium supplemented with 0.5 mg/ml Geneticin and 10% dialyzed FCS, the antigen binding activity of the humanized 2K1 antibody contained in the culture was assayed by ELISA. First, sandwich ELISA using the goat-derived anti-human IgG Fc antibody (CAPPEL) and protein A-HRP (ZYMED LABORATORIES, INC.) was done to measure the concentration of the humanized 2K1 antibody contained in the culture medium. In this case, a dilution series of a commercially available human IgG1 antibody (Biogenesis) was prepared and used as a standard sample. Additionally, the concentration of the chimera 2K1 antibody was also measured by the ELISA described above.

Example 14

Confirmation of the Binding Activities of the Chimera 2K1 Antibody and the Humanized 2K1 Antibody with Osteopontin Peptide:

Based on the concentrations of the humanized 2K1 antibody and the chimera 2K1 antibody as determined in Example 13, the binding activities of the humanized 2K1 antibody and the chimera 2K1 antibody with osteopontin peptide (CVDTYDGRGDSVVYGLRS) (SEQ ID NO: 1) were compared with reference to the ELISA of Kon et al. (Journal of Cellular Biology, 88: 420–432 (2002)).

Dilution series of the humanized 2K1 antibody and the chimera 2K1 antibody reacted on a microtiter plate with BSA-crosslinked osteopontin peptide (BSA-CVDTYDGRGDSVVYGLRS)(SEQ ID NO: 1) immobilized thereon. Then, the antibodies bound to BSA-CVDTYDGRGDSVVYGLRS (SEQ ID NO: 1) reacted with protein A-HRP, and finally with TMB (Dojindo Corporate), to measure the absorbance at a wavelength of 450 nm.

Additionally, reaction on a plate with only BSA immobilized thereon as a negative control was also measured in the same manner. These results are shown in FIG. 13.

Figure 13:
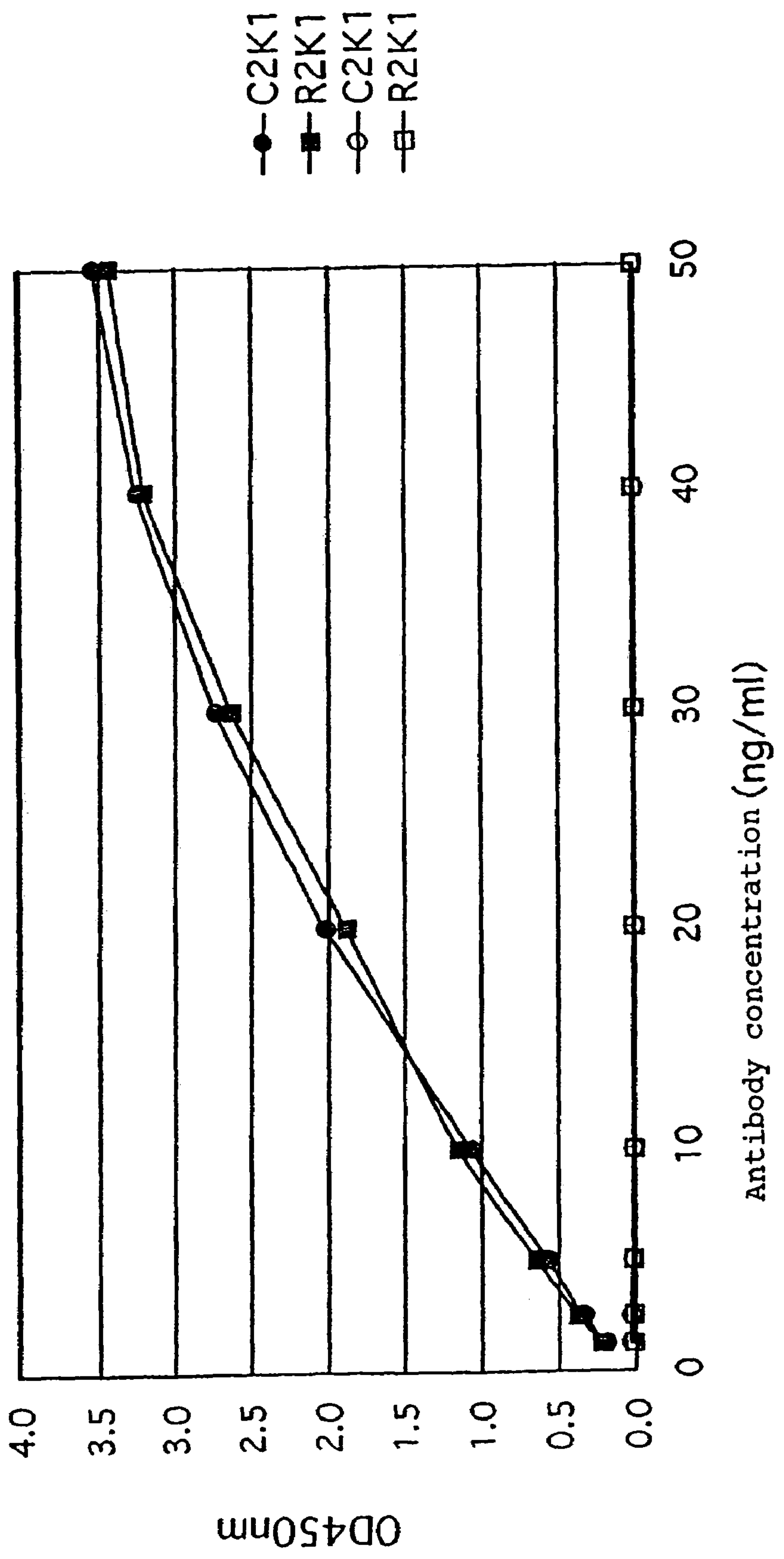
FIG. 13 shows graphs depicting the binding activities of various concentrations of the humanized 2K1 antibody and the chimera 2K1 antibody to the osteopontin peptide.

The axis of abscissa shows the concentration of the antibodies, while the axis of ordinate shows absorbance in FIG. 13, where solid circle shows the binding activity of the chimera 2K1 antibody to BSA-CVDTYDGRGDSVVYGLRS (SEQ ID NO: 1), while solid square shows the binding activity of the humanized 2K1 antibody to BSA-CVDTYDGRGDSVVYGLRS (SEQ ID NO: 1). As a negative control, additionally, the binding activity of the chimera 2K1 antibody to BSA (open circle) and the binding activity of the humanized 2K1 antibody to BSA (open square) are also shown.

Consequently, it is shown that the humanized 2K1 antibody and the chimera 2K1 antibody had binding activities only to BSA-CVDTYDGRGDSVVYGLRS (SEQ ID NO: 1), not to BSA. Thus, it is shown that the binding activities of these antibodies are specific to osteopontin peptide. Additionally, the binding activities of both the antibodies to BSA-CVDTYDGRGDSVVYGLRS (SEQ ID NO: 1) are at the same level.

As described above, the chimera 2K1 antibody and the original murine 2K1 antibody have the same level of antigen binding activity. Thus, it is clearly shown that the humanized 2K1 antibody prepared in accordance with the invention has an antigen binding activity identical to that of the original murine 2K1 antibody.

Example 15

Preparation of M5 Antibody:

The following synthetic peptide corresponding to the inner sequence (C+V138 to R153) of murine OPN was prepared for use in immunization.

```
M5 peptide:
CVDVPNGRGDSLAYGLR
```

The peptide was bound to thyroglobulin, for subsequent use for rabbit immunization according to a general method. Anti-serum was collected from the immunized rabbit, to prepare the M5 antibody, using a column packed with the M5 peptide of the N terminal cysteine bound through disulfide bond to thiol Sepharose beads (Amersham Pharmacia Biotech, Tokyo, Japan).

Example 16

Reactivity of the M5 Antibody with Opn and the Thrombin Digestion Products Thereof:

The binding potency of the M5 antibody recovered in Example 15 with OPN and the thrombin digestion products thereof was tested by the Western blotting method. Recombinant murine OPN of the glycosylated form as generated in CHO cells was used as the OPN. The M5 antibody reacted with OPN and the thrombin digestion products thereof.

Example 17

Inhibition of Cell Adhesion to OPN Via the M5 Antibody:

It was examined by the method described in the reference (S. Kon et al., (2002): J. Cell. Biochem., 84(2), 420–432) as to whether or not the M5 antibody might inhibit cell adhesion to OPN. As the OPN, the full-length murine OPN was used, from which the GST segment had preliminarily been removed with PreScission protease (Amersham Pharmacia Biotech, Tokyo, Japan) (referred to as "mOPN/de-GST" hereinafter) was used. As the cell, murine NIH 3T3 cell was used.

Figure 14:
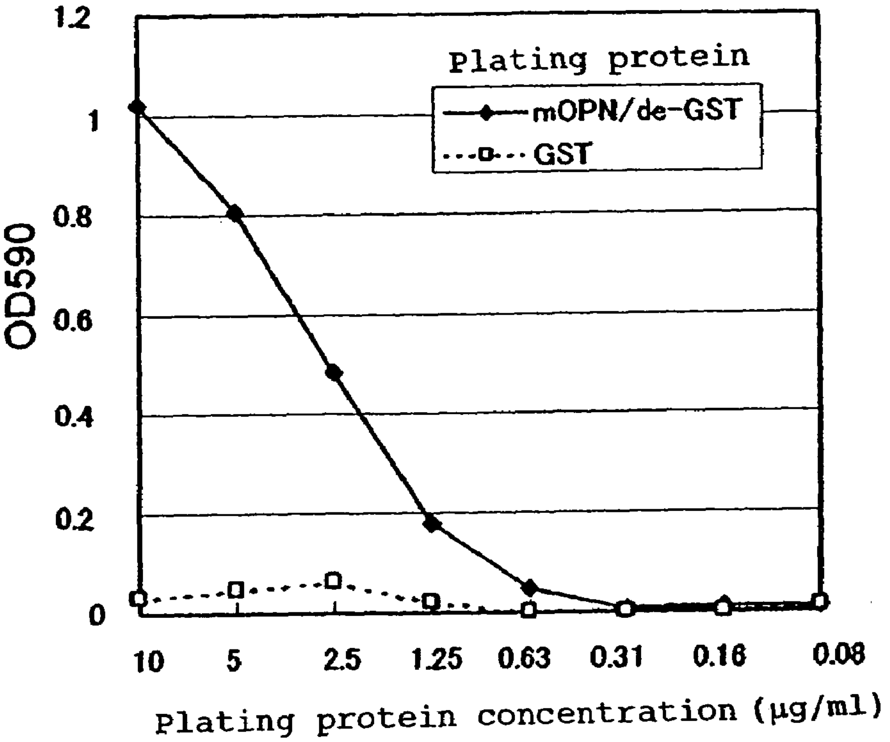
FIG. 14 shows graphs depicting the concentration-dependent adhesion of the murine OPN to NIH 3T3.
Figure 15:
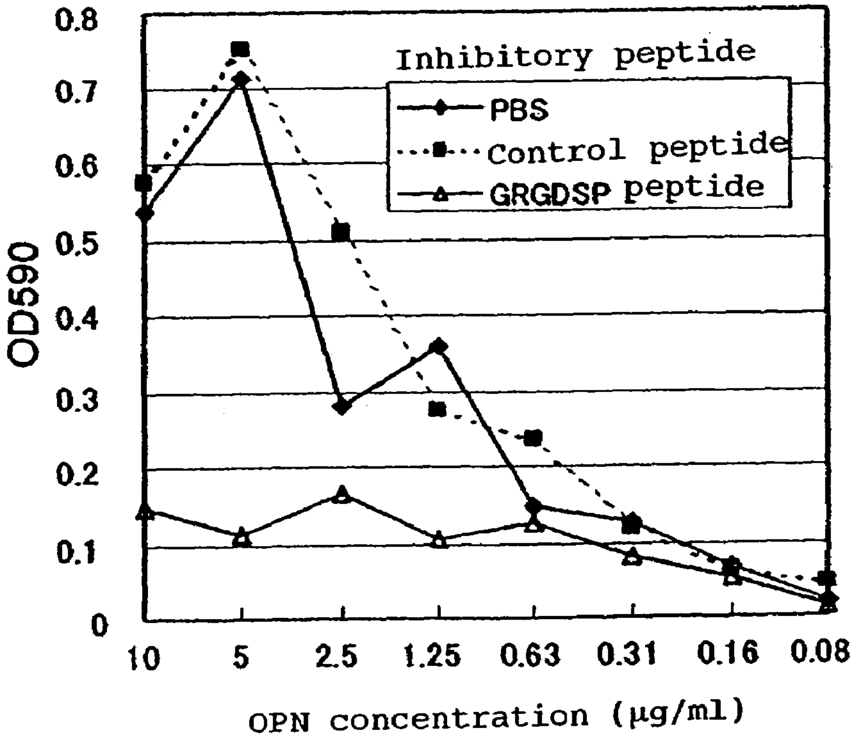
FIG. 15 shows graphs depicting the inhibition of the adhesion of the murine OPN to NIH 3T3 with the GRGDSP (SEQ ID NO: 55) peptide.
Figure 16:
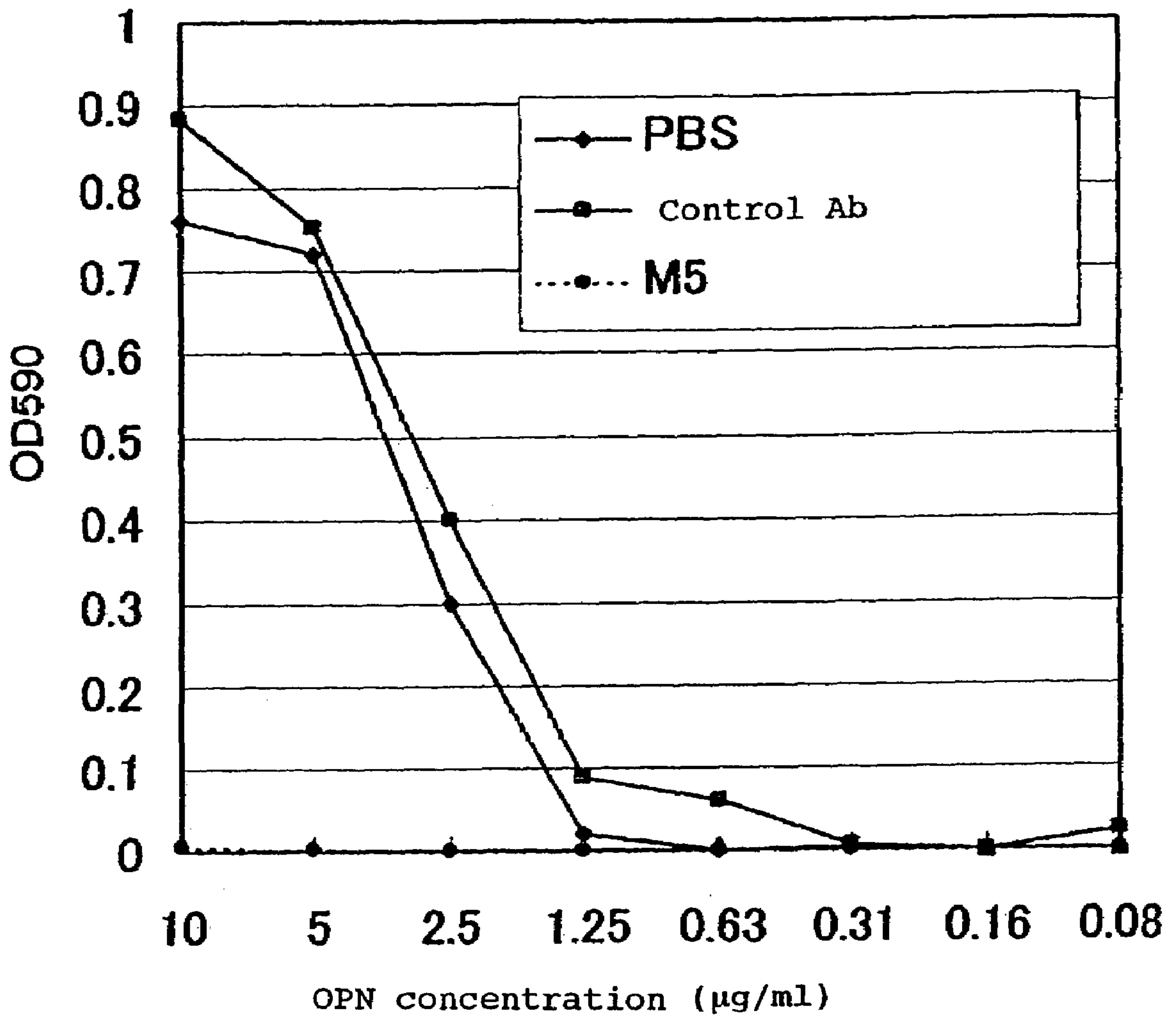
FIG. 16 shows graphs depicting the inhibition of the adhesion of the murine OPN to NIH 3T3 with the M5 antibody.

As shown in FIG. 14, the NIH 3T3 cell adheres to mOPN/dc-GST in a concentration-dependent manner. As shown in FIG. 15, further, the adhesion is apparently inhibited by the peptide GRGDSP (SEQ ID NO: 55) (100 μg/mL), so the adhesion depends on RGD. As shown in FIG. 16, the M5 antibody at 200 μg/mL apparently inhibited cell adhesion to OPN.

Example 18

Inhibitory Activity of the M5 Antibody Against Murine Spleen-Derived Monocyte Migration:

The inhibitory activity of the M5 antibody against cytokine-activated murine spleen-derived monocyte migration was examined by the following method. The results are shown in Table 4.

<Experimental Method>

The splenocyte from C57BL/6 mouse was ground on a slide glass into a single cell, which was then cultured in a flask at 37° C. for one hour. The resulting adherent cell was used as monocyte. The monocyte was overnight cultured and activated with human TNF-α (20 ng/mL). The resulting activated monocyte was used at a migration experiment. The migration experiment was done by the same method as for the human sample in Example 6 above.

<Experimental Results>

The M5 antibody inhibited the migration of TNF-α-activated monocyte derived from murine spleen toward the thrombin-cleavage-type murine OPN recovered from cleavage of the full-length murine OPN (manufactured by Genzyme Corporation) with bovine thrombin (manufactured by Sigma).

TABLE 4

| Concentration of thrombin-cleavage-type murine OPN (μg/mL) | M5 concentration (μg/mL) | Mean migrating cell counts per 1 $mm^3$ |
|---|---|---|
| 0 | 0 | 428.3 ± 52.7* |
| 10 | 0 | 556.7 ± 46.3 |
| 10 | 0.8 | 570.0 ± 75.6 |
| 10 | 4 | 536.7 ± 60.6 |
| 10 | 20 | 461.7 ± 104.4 |
| 10 | 100 | 468.3 ± 67.9 |

*$P < 0.05$ (one way ANOVA, Dunnett's test)

Example 19

Action of the M5 Antibody on Bone Damage Suppression:

By the following method, the action of the M5 antibody on bone damage suppression in a murine calvaria organ culture system was examined. The results are shown in Table 5.

<Experimental Method>

From a newborn mouse on day 1 after birth was resected the cranial bone; after size adjustment, a half thereof was placed in each well of a 24-well plate. To each well was then added human parathyroid hormone (PTH) (1–34) adjusted with addition of a D-MEM culture broth (with 10% bovine serum added) to a final PTH concentration of 10 nM, to induce bone damage. The M5 antibody was added to a final concentration of 200 μg/mL. After culturing at 37° C. for one week, the quantity of calcium released from bone into the culture broth was assayed by Calcium E Test WAKO (Wako Pure Chemical Industries, Ltd.).

<Experimental Results>

With no PTH addition, calcium was at a value of 7.02 mg/mL. With PTH addition, however, calcium was at a value of 9.11 mg/mL. Hence, it was observed that calcium release from bone was promoted. When the M5 antibody was added at a concentration of 200 μg/mL, it was verified that bone absorption was inhibited by about 70%.

TABLE 5

| | Quantity of calcium released (mg/dL) |
|---|---|
| Medium | 7.02 ± 0.18** |
| PTH control | 9.11 ± 0.17 |
| M5 | 7.65 ± 0.25** |

**P < 0.01 (one way ANOVA, Dunnett's test)

Example 20

Effect of M5 Antibody in Mouse Collagen Arthritis Model:

By the following method, the effect of the M5 antibody in a mouse collagen arthritis model was examined. Table 6 shows the results about arthritis score; Table 7 shows the results about leg edema; Table 8 shows the results about body weight change; and Table 9 shows the results about the change of feed intake.

<Experimental Method>

For arthritis induction, an arthritogenic antibody cocktail (under the trade name of a cocktail for arthritis, Arthrogen-CIA® mAb, Arthritogenic mAb cocktail; manufactured by Iwai Chemical Pharmaceutical Co., Ltd.) recognizing four epitopes specific to collagen was used. To a mouse was intravenously administered the arthritogenic cocktail; 3 days later, LPS (100 μg) was intraperitoneally administered to thereby elicit arthritis. Arthritis was observed on day 3 after LPS dosing, which reached maximum on day 6.

Immediately before LPS dosing and 3 days later, the M5 antibody was intravenously administered at a dose of 40 μg, 150 μg or 400 μg. As the control group, a rabbit IgG-dosed group (at a dose of 400 μg) was arranged. Additionally, the anti-mouse TNF-α antibody was intravenously administered at a dose of 200 μg/mouse immediately before LPS administration and 3 days later. As the control group, a rat IgG-dosed group (at a dose of 200 μg) was arranged. Further, MTX was orally given (at a dose of 3.2 mg/kg) once daily on the very day of LPS dosing and thereafter. Then, MTX dissolved in 5 ml of 0.5% methyl cellulose solution was used. For the control group, 5 ml of 0.5% methyl cellulose solution was arranged.

Concerning four items, namely arthritis score, leg edema, body weight change and feed intake, assessment was done per each group of five animals.

<Experimental Results>

As shown in Tables 6 to 9, the M5 antibody exerted distinct suppressive actions on the improvement of arthritis score, the delay of the onset of arthritis, and the improvement of leg edema in the mouse arthritis model (therapeutic effect). The onset of arthritis was suppressed in a concentration-dependent manner at a level such that the effect exceeded the effect of the anti-mouse TNF-α antibody dosed (at a dose of 200 μg/mouse). In contrast, MTX exerted almost no pharmaceutical efficacy.

In the normal group of the model, furthermore, distinct body weight decrease by about 3 g was observed in 3 days after LPS dosing; and the tendency was continued on day 3 to day 6, although the decrease ratio was more or less reduced. In the groups dosed with the M5 antibody (150 μg, 400 μg) and the group dosed with the anti-mouse TNF-α antibody, alternatively, apparent improvement of body weight decrease was observed. Concerning the feed intake, furthermore, rapid body weight decrease was observed for any of the pharmaceutical substances up to day 3 after LPS dosing; on day 3 to day 6, however, the decrease was improved in the groups dosed with the M5 antibody and the group dosed with the anti-mouse TNF-α antibody. Table 6 shows the effect on arthritis score; Table 7 shows the suppressive effect on leg edema; Tables 8 and 9 show the effects on body weight change and feed intake change, respectively.

TABLE 6

| Days | Rabbit IgG-dosed group (dose; 400 μg/mouse) | M5 antibody-dosed group(dose; μg/mouse) 40 | 150 | 400 |
|---|---|---|---|---|
| 3 | 1.2 ± 1.1 | 2.4 ± 1.7 | 1.0 ± 1.2 | 0.0 ± 0.0 |
| 4 | 1.8 ± 1.3 | 3.4 ± 1.1 | 1.4 ± 0.5 | 0.2 ± 0.4* |
| 5 | 5.0 ± 1.6 | 6.0 ± 2.0 | 3.0 ± 1.2* | 1.8 ± 0.4** |
| 6 | 5.4 ± 1.3 | 7.2 ± 1.3 | 4.6 ± 1.5 | 3.0 ± 1.0* |

**P < 0.01,
*P < 0.05 (non-parametric Mann-Whitney test)

| Days | Rat IgG-dosed group (dose; 200 μg/mouse) | Anti-mouse TNF-α antibody-dosed group (dose; 200 μg/mouse) |
|---|---|---|
| 3 | 0.8 ± 0.4 | 1.0 ± 0.6 |
| 4 | 2.4 ± 0.2 | 1.0 ± 0.5 |
| 5 | 5.8 ± 0.4 | 3.2 ± 0.5* |
| 6 | 6.6 ± 0.4 | 5.8 ± 0.5 |

*P < 0.05 (non-parametric Mann-Whitney test)

| Days | Control group | MTX-dosed group (dose; 3.2 mg/kg) |
|---|---|---|
| 3 | 1.0 ± 0.3 | 0.8 ± 0.4 |
| 4 | 1.8 ± 0.6 | 1.8 ± 0.7 |
| 5 | 4.0 ± 0.9 | 6.0 ± 0.6 |
| 6 | 5.2 ± 0.9 | 6.0 ± 0.6 |

TABLE 7

| Site | Volume of leg edema (mL) Normal group | Rabbit IgG-dosed group (dose; 400 μg/mouse) | M5-dosed group (dose; μg/mouse) 40 | 150 | 400 |
|---|---|---|---|---|---|
| Foreleg | 0.041 ± 0.003** | 0.051 ± 0.004 | 0.055 ± 0.004 | 0.041 ± 0.004** | 0.038 ± 0.001** |
| Hind leg | 0.117 ± 0.004** | 0.138 ± 0.005 | 0.140 ± 0.010 | 0.127 ± 0.006 | 0.121 ± 0.009** |

| Site | Volume of leg edema (mL) Normal group | Rat IgG-dosed group (dose; 200 μg/mouse) | Anti-mouse TNF-α antibody-dosed group (dose; 200 μg/mouse) |
|---|---|---|---|
| Foreleg | 0.041 ± 0.003** | 0.044 ± 0.003 | 0.041 ± 0.002 |
| Hind leg | 0.117 ± 0.004** | 0.127 ± 0.004 | 0.130 ± 0.006 |

| Site | Volume of leg edema (mL) Normal group | Control group | MTX-dosed group (dose; 3.2 mg/kg) |
|---|---|---|---|
| Foreleg | 0.041 ± 0.003** | 0.044 ± 0.002 | 0.047 ± 0.003 |
| Hind leg | 0.117 ± 0.004** | 0.129 ± 0.005 | 0.132 ± 0.003 |

**P < 0.01,
*P < 0.05 (one way ANOVA, Dunnett's test)

TABLE 8

| | Body weight change (g) | | | | |
|---|---|---|---|---|---|
| | Normal group | Rabbit IgG-dosed group (dose; 400 μg/mouse) | M5-dosed group (dose; μg/mouse) 40 | 150 | 400 |
| On day 0 to day 3 post-dosing | 0.1 | −2.8 | −2.4 | −1.6 | −1.5 |
| On day 3 to day 6 post-dosing | 0.5 | 1.8 | 1.0 | 0.8 | 1.5 |

| | Body weight change (g) | | |
|---|---|---|---|
| | Normal group | Rat IgG-dosed group (dose; 200 μg/mouse) | Anti-mouse TNF-α antibody-dosed group (dose; 200 μg/mouse) |
| On day 0 to day 3 post-dosing | 0.1 | −2.9 | −1.7 |
| On day 3 to day 6 post-dosing | 0.5 | −1.7 | −0.1 |

| | Body weight change (g) | | |
|---|---|---|---|
| | Normal group | Control group | MTX-dosed group (dose; 3.2 mg/kg) |
| On day 0 to day 3 post-dosing | 0.1 | −2.9 | −1.5 |
| On day 3 to day 6 post-dosing | 0.5 | −2.7 | −1.8 |

TABLE 9

| | Quantity of feed intake (g/mouse/day) | | | | |
|---|---|---|---|---|---|
| | Normal group | Rabbit IgG-dosed group (dose; 400 μg/mouse) | M5-dosed group (dose; μg/mouse) 40 | 150 | 400 |
| On day 0 to day 3 post-dosing | 2.7 | 1.0 | 0.9 | 1.4 | 1.1 |
| On day 3 to day 6 post-dosing | 2.9 | 2.4 | 2.3 | 2.4 | 2.8 |

| | Quantity of feed intake (g/mouse/day) | | |
|---|---|---|---|
| | Normal group | Rat IgG-dosed group (dose; 200 μg/mouse) | Anti-mouse TNF-α antibody-dosed group (dose; 200 μg/mouse) |
| On day 0 to day 3 post-dosing | 2.7 | 1.0 | 1.3 |
| On day 3 to day 6 post-dosing | 2.9 | 2.5 | 2.8 |

| | Quantity of feed intake (g/mouse/day) | | |
|---|---|---|---|
| | Normal group | Control group | MTX-dosed group (dose; 3.2 mg/kg) |
| On day 0 to day 3 post-dosing | 2.7 | 0.9 | 0.8 |
| On day 3 to day 6 post-dosing | 2.9 | 2.4 | 2.1 |

Example 21

Availability of OPN-Related Fragment Peptides:

OPN-related fragment peptides at a state purified by HPLC chromatography were purchased from Auspep Inc., Parkiville, Australia. The amino acid sequences thereof are shown in (1) to (3).

```
hOPN5:
CVDTYDGRGDSVVYGLRS (C + V153 to S169)        (1)

hOPN3:
KSKKFRRPDIQYPDATDEC (K170 TO E187 + C)       (2)

hOPN1:
IPVKQADSGSSEEKQC (117 to Q31 + C)            (3)
```

Example 22

Preparation of Antigens for Immunization:

Products of the OPN-related fragment peptides bound to thyroglobulin were prepared as immunogens by the EMCS (N-(6-maleimidocaproyloxy)-succinimide) process, as follows. For preparation of such products, the molar ratio of thyroglobulin, an OPN-related fragment peptide and EMCS was 1:300:400.

4 mg of each of the OPN-related fragment peptides in Example 21 was dissolved in distilled water of about 1 ml. Alternatively, 5 mg thyroglobulin dissolved in 1 ml of 0.01 M phosphate buffer, pH 7.0 and EMCS dissolved at 80 μg/μl in dimethylformamide were mixed together, individually at quantities corresponding to the moles, to prepare a thyroglobulin-EMCS complex solution. The complex solution was divided in three portions. To each of the portions was added the OPN-related fragment peptide solution at a quantity corresponding to the mole, to thereby prepare a solution of an EMCS-crosslinked product of the OPN-related fragment peptide bound to thyroglobulin.

The solution of such bound product was dialyzed, using PBS, to adjust the concentration of the bound product to 10 μg/μl. The bound product of the OPN-related fragment peptide and thyroglobulin was used as an antigen for immunization.

Example 23

Preparation of Antigens for Screening:

As OPN proteins for screening, fusion proteins between GST and human OPN isoforms, namely GST-OPN-a, GST-OPN-b and GST-OPN-c, and fusion proteins between GST and the OPN fragment on the side of amino group (GST-N half) from the thrombin cleavage site and the OPN fragment on the side of carboxyl group (GST-C half) from the same thrombin cleavage site were prepared by the method described in Example 1, for use in the anti-serum reactivity with OPN.

Example 24

Immune Sensitization:

Rabbit was immunized, using as antigens for immunization, the bound products of the OPN-related fragment peptides and thyroglobulin prepared in Example 22. Immunization was done, by boosting 100 μl (100 μg) of a bound product solution every one week or every two weeks. The antigens were mixed with the Freund complete adjuvant for the first immunization and were then mixed with the Freund incomplete adjuvant for the second immunization and the following immunizations. After eight times of immunization, serum was separated from collected blood, which was then used as anti-serum.

Example 25

Reactivity of Anti-Sera with OPN:

The OPN-related fragment peptides prepared in Example 21 were diluted with 0.1 M carbonate buffer, pH 9.5 to 10 μg/ml, which were then immobilized at 50 μl/well on a 96-well plate.

After rinsing with PBS and blocking with 0.1% BSA/PBS/0.05% $NaN_3$ solution, a 2-fold dilution series of the 100-fold dilution of the anti-sera recovered in Example 24 was placed at 50 μl in a well, for reaction at 37° C. for 30 minutes.

After termination of the reaction, the well was rinsed four times with 0.05% Tween 20-PBS. Then, 50 μl each of HRP-labeled anti-rabbit IgG (manufactured by IBL Co., Ltd.) was added to each well, for reaction at 37° C. for 30 minutes. After termination of the reaction, 100 μl each of 0.05 M citrate buffer, pH 4.5 containing 0.4 mg/ml orthophenylenediamine (OPD) and aqueous 0.03% hydrogen peroxide was added to each well. Then, the plate was left to stand in darkness at ambient temperature for 15 minutes, for chromogenic reaction. After the chromogenic reaction, 100 μl of 1N sulfuric acid was added to each well, to terminate the reaction, for absorbance measurement at 492 nm.

Using the OPN proteins prepared in Example 23, alternatively, the reactivity of the anti-sera was examined by Western blotting method. Consequently, anti-sera against the OPN-related fragment peptides hOPN1 and hOPN5 reacted with GST-OPN-a, GST-OPN-b, GST-OPN-c and GST-N half, but never reacted with GST-C half. Alternatively, anti-serum against the OPN-related fragment peptide hOPN3 reacted with GST-OPN-a, GST-OPN-b, GST-OPN-c and GST-C half, but never reacted with GST-N half.

Example 26

Preparation of HRP-Bound Products of Anti-OPN-Related Fragment Peptides Antibodies:

HRP-bound products of the antibodies against the OPN-related fragment peptides hOPN3 and hOPN1 were prepared as follows. 20 mg of each anti-OPN-related fragment peptide antibody was digested with pepsin, followed by gel filtration to purify the $F(ab')_2$ fragment of the anti-OPN-related fragment peptide antibody. Then, the $F(ab')_2$ fragment was reduced to Fab' fragment, by using 2-mercaptoethanol. HRP reacted with EMCS at 37° C. for 60 minutes, followed by gel filtration to prepare a HRP-EMCS bound product, which further reacted with the anti-OPN-related fragment peptide antibody Fab' fragment at 4° C. overnight, followed by gel filtration to prepare an EMCS-crosslinked HRP-bound product of the anti-OPN-related fragment peptide antibody.

Example 27

Construction of Sandwich ELISA Systems:

From combinations of a sandwich ELISA plate and labeled antibodies, two types of systems namely 1-3 and 5-1 were prepared. Specifically, the 1-3 system was prepared as follows. The 10 μg/ml antibody against the OPN-related fragment peptide hOPN1 was added in 100 μl portions to a 96-well ELISA plate. After overnight reaction at 4° C., blocking with 10% BSA/PBS/$NaN_3$ solution was done. The resulting plate at that state was used as the sandwich ELISA plate. The HRP-bound product of the antibody against the OPN-related fragment peptide hOPN3 prepared in Example 26 was defined as labeled antibody. As described above, a combination between the immobilizing plate using the antibody against hOPN1 and the labeled antibody using the antibody against hOPN3 was defined as system 1-3.

In the same manner, a combination of an immobilizing plate using the antibody against hOPN5 and a labeled antibody using the antibody against hOPN1 was constructed as system 5-1.

Example 28

Osteopontin Assay in a Test Subject by Sandwich ELISA Systems:

The OPN protein was assayed as follows. 100 μl of a solution containing a plasma sample or an articular cavity fluid sample from a test subject was added to the sandwich ELISA plates of the systems 1-3 and 5-1, for reaction at 37° C. for one hour. After reaction, the plates were rinsed four times with 0.05% Tween 20-PBS, followed by addition of 100 μl each of the labeled antibodies specific to the individual systems for reaction at 4° C. for 30 minutes. After reaction, the plates were rinsed six times with 0.05% Tween 20-PBS, followed by addition of 100 μl of a TMB (tetramethylbenzidine) solution. Then, the resulting plates were left to stand in darkness at ambient temperature for 30 minutes. 1N sulfuric acid was used to terminate the reaction, for the assay of the absorbance at 450 nm.

Table 10 shows the OPN values in the articular cavity fluids of patients (13 cases) with rheumatism as measured by the method; and Table 11 shows the OPN values in the articular cavity fluids of patients (12 cases) with osteoarthritis. Additionally, Table 12 shows the OPN values in the plasmas from rheumatism patients (16 cases); Table 13 shows the OPN values in the plasmas from osteoarthritis patients (7 cases); and Table 14 shows the OPN values in the plasmas from normal subjects (6 cases).

As apparently shown in these results, the comparison with the system 1-3 in terms of plasma OPN value among the patients with rheumatoid arthritis, the patients with osteoarthritis, and the normal subjects did not make any significant difference. However, the comparison with the system 5-1 in terms of plasma OPN value among the patients with rheumatoid arthritis, the patients with osteoarthritis, and the normal subjects showed significantly higher plasma OPN values in the patients with rheumatoid arthritis and the patients with osteoarthritis than the OPN value in the normal subjects. The level of significance was higher in the patients with rheumatoid arthritis. This indicates that total OPN quantity reflected with the system 5-1 is effective for the diagnosis of the general category of arthritis.

Alternatively, OPN values in the articular cavity fluids of the patients with rheumatoid arthritis and the patients with osteoarthritis are larger than the OPN values in the plasmas thereof, which strongly indicates local OPN generation.

Additionally, the comparison with any of the systems 1-3 and 5-1 in terms of OPN value of articular cavity fluid between the patients with rheumatoid arthritis and the patients with osteoarthritis showed that the OPN value in the patients with rheumatoid arthritis was significantly larger than the OPN value in the patients with osteoarthritis.

As a new indicator, the ratio of OPN values with the systems 1-3 and 5-1 was examined. The indicator can be used for the comparison of the ratio of the thrombin-cleaved OPN. The OPN values in the plasmas and articular cavity fluids from rheumatoid arthritis patients were 1 or less, and the OPN values from osteoarthritis patients were 2 or more. Therefore, a significant difference was observed. Thus, the OPN values with the systems 1-3/5-1 can be used for a diagnostic method for discriminating rheumatoid patients from osteoarthritis patients at an early stage.

TABLE 10

| Sample | System 1-3 (ng/ml) | System 5-1 (ng/ml) | System 1-3/system 5-1 |
|---|---|---|---|
| RA 1 | 8498 | 2932 | 2.898 |
| RA 2 | 22715 | 26223 | 0.866 |
| RA 3 | 2659 | 1905 | 1.396 |
| RA 4 | 20186 | 94430 | 0.214 |
| RA 5 | 1520 | 2002 | 0.759 |
| RA 6 | 5870 | 2238 | 2.623 |
| RA 7 | 7303 | 56753 | 0.129 |
| RA 8 | 2200 | 6268 | 0.351 |
| RA 9 | 18344 | 59873 | 0.306 |
| RA 10 | 2133 | 2002 | 1.065 |
| RA 11 | 26804 | 33036 | 0.811 |
| RA 12 | 18868 | 32824 | 0.575 |
| RA 13 | 3633 | 6067 | 0.599 |
| Mean | 10825.6 | 25119.5 | 0.969 |

TABLE 11

| Sample | System 1-3 (ng/ml) | System 5-1 (ng/ml) | System 1-3/system 5-1 |
|---|---|---|---|
| OA 1 | 1520 | 3471 | 0.438 |
| OA 2 | 9957 | 14374 | 0.693 |
| OA 3 | 6595 | 2932 | 2.249 |
| OA 4 | 3523 | 237 | 14.865 |
| OA 5 | 8619 | 28483 | 0.303 |
| OA 6 | 1926 | 896 | 2.150 |
| OA 7 | 653 | 850 | 0.768 |
| OA 8 | 6490 | 7814 | 0.831 |
| OA 9 | 4750 | 1987 | 2.391 |
| OA 10 | 6830 | 2932 | 2.329 |
| OA 11 | 386 | 181 | 2.133 |
| OA 12 | 1621 | 356 | 4.553 |
| Mean | 4405.8 | 5376.1 | 2.808 |

TABLE 12

| Sample | System 1-3 (ng/ml) | System 5-1 (ng/ml) | System 1-3/system 5-1 |
|---|---|---|---|
| RA 1 | 1621 | 1379 | 1.175 |
| RA 2 | 532 | 845 | 0.630 |
| RA 3 | 132 | 617 | 0.214 |
| RA 4 | 142 | 1758 | 0.081 |
| RA 5 | 624 | 2089 | 0.299 |
| RA 6 | 341 | 1990 | 0.171 |
| RA 7 | 152 | 845 | 0.180 |
| RA 8 | 671 | 224 | 2.996 |
| RA 9 | 543 | 557 | 0.975 |
| RA 10 | 947 | 431 | 2.197 |
| RA 11 | 935 | 1794 | 0.521 |
| RA 12 | 1008 | 1650 | 0.611 |
| RA 13 | 636 | 678 | 0.938 |
| RA 14 | 464 | 545 | 0.851 |
| RA 15 | 683 | 488 | 1.400 |
| RA 16 | 1057 | 597 | 1.771 |
| Mean | 6555 | 1030.4 | 0.938 |

TABLE 13

| Sample | System 1-3 (ng/ml) | System 5-1 (ng/ml) | System 1-3/system 5-1 |
|---|---|---|---|
| OA 1 | 695 | 302 | 2.301 |
| OA 2 | 1094 | 412 | 2.655 |
| OA 3 | 1070 | 557 | 1.921 |
| OA 4 | 75 | 1129 | 0.066 |
| OA 5 | 814 | 356 | 2.286 |
| OA 6 | 959 | 276 | 3.475 |
| OA 7 | 983 | 311 | 3.161 |
| Mean | 812.9 | 477.6 | 2.267 |

TABLE 14

| Sample | System 1-3 (ng/ml) | System 5-1 (ng/ml) | System 1-3/ system 5-1 |
|---|---|---|---|
| Normal 1 | 475 | 199 | 2.387 |
| Normal 2 | 578 | 249 | 2.321 |
| Normal 3 | 802 | 232 | 3.457 |
| Normal 4 | 983 | 384 | 2.560 |
| Normal 5 | 520 | 284 | 1.831 |
| Normal 6 | 624 | 215 | 2.902 |
| Mean | 663.7 | 260.5 | 2.576 |

The invention claimed is:

1. A chimeric anti-osteopontin antibody, which inhibits the binding between a thrombin-cleaved N-terminal fragment of osteopontin and:

an integrin recognizing the site of amino acid sequence RGD, and an integrin recognizing the site of amino acid sequence SVVYGLR (residues 11–17 of SEQ ID NO: 1);

wherein said antibody has a heavy chain variable region having an amino acid sequence of SEQ ID NO: 19 and light chain variable region having an amino acid sequence of SEQ ID NO: 20.

2. The chimeric anti-osteopontin antibody according to claim 1, wherein the heavy chain constant region in the antibody is human Igγ1.

3. The chimeric anti-osteopontin antibody according to claim 1, wherein the light chain constant region in the antibody is human Igκ.

4. A humanized anti-osteopontin antibody, wherein said antibody inhibits the binding between a thrombin-cleaved N-terminal fragment of osteopontin and:

an integrin recognizing the site of amino acid sequence RGD, and an integrin recognizing the site of amino acid sequence SVVYGLR (residues 11–17 of SEQ ID NO: 1);

wherein said antibody has heavy chain CDR1, CDR2 and CDR3 having an amino acid sequence of SEQ ID NOS: 21, 22 and 23 respectively, and light chain CDR1, CDR2 and CDR3 having an amino acid sequence of SEQ ID NOS: 24, 25 and 26 respectively.

5. The humanized anti-osteopontin antibody according to claim 4, wherein said antibody has heavy chain variable region having an amino acid sequence of SEQ ID NO: 28 and light chain variable region having an amino acid sequence of SEQ ID NO: 30.

6. The humanized anti-osteopontin antibody according to claim 4, wherein the heavy chain constant region in the antibody is human Igγ1.

7. The humanized anti-osteopontin antibody according to claim 4, wherein the light chain constant region in the antibody is human Igκ.

* * * * *

SEQUENCE LISTING

```
<160> NUMBER OF SEQ ID NOS: 50

<210> SEQ ID NO 1
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 1

Cys Val Asp Thr Tyr Asp Gly Arg Gly Asp Ser Val Val Tyr Gly Leu
1               5                   10                  15

Arg Ser
```

-continued

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 2

Lys Ser Lys Lys Phe Arg Arg Pro Asp Ile Gln Tyr Pro Asp Ala Thr
1               5                   10                  15

Asp Glu Cys

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 3

Ile Pro Val Lys Gln Ala Asp Ser Gly Ser Ser Glu Glu Lys Gln Cys
1               5                   10                  15

<210> SEQ ID NO 4
<211> LENGTH: 35
<212> TYPE: DNA
<213> ORGANISM: Artificial Sequence
<220> FEATURE:
<223> OTHER INFORMATION: Synthetic DNA

<400> SEQUENCE: 4
cgggatccac taccatgaga attgcagtga tttgc 35

<210> SEQ ID NO 5
<211> LENGTH: 36
<212> TYPE: DNA
<213> ORGANISM: Artificial Sequence
<220> FEATURE:
<223> OTHER INFORMATION: Synthetic DNA

<400> SEQUENCE: 5
ccgctcgagt taattgacct cagaagatgc actatc 36

<210> SEQ ID NO 6
<211> LENGTH: 37
<212> TYPE: DNA
<213> ORGANISM: Artificial Sequence
<220> FEATURE:
<223> OTHER INFORMATION: Synthetic DNA

<400> SEQUENCE: 6
acacagcatt cttttccaca gaacttccag aatcagc 37

<210> SEQ ID NO 7
<211> LENGTH: 35
<212> TYPE: DNA
<213> ORGANISM: Artificial Sequence
<220> FEATURE:
<223> OTHER INFORMATION: Synthetic DNA

<400> SEQUENCE: 7
tgaggaaaag aatgctgtgt cctctgaaga aaacc 35

<210> SEQ ID NO 8
<211> LENGTH: 32
<212> TYPE: DNA

-continued

<213> ORGANISM: Artificial Sequence
<220> FEATURE:
<223> OTHER INFORMATION: Synthetic DNA

<400> SEQUENCE: 8
gcctcgagtt acctcagtcc ataaaccaca ct 32

<210> SEQ ID NO 9
<211> LENGTH: 31
<212> TYPE: DNA
<213> ORGANISM: Artificial Sequence
<220> FEATURE:
<223> OTHER INFORMATION: Synthetic DNA

<400> SEQUENCE: 9
tcttagattt ggcacaggtg atgcctagga g 31

<210> SEQ ID NO 10
<211> LENGTH: 31
<212> TYPE: DNA
<213> ORGANISM: Artificial Sequence
<220> FEATURE:
<223> OTHER INFORMATION: Synthetic DNA

<400> SEQUENCE: 10
cacctgtgcc aaatctaaga agtttcgcag a 31

<210> SEQ ID NO 11
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 11

Cys Val Asp Thr Tyr Asp Gly Arg Gly Asp Ser Val Val Tyr Gly Leu
1 5 10 15

Arg Ser

<210> SEQ ID NO 12
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 12

Cys Ile Asp Ser Gln Glu Leu Ser Lys Val Ser Arg Glu Phe His Ser
1 5 10 15

His

<210> SEQ ID NO 13
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 13

Cys Val Asp Val Pro Asn Gly Arg Gly Asp Ser Leu Ala Tyr Gly Leu
1 5 10 15

Arg

<210> SEQ ID NO 14

-continued

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Ser Val Val Tyr Gly Arg Leu
1               5


<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 15

Arg Gly Asp Ser Val Val Tyr Gly Leu Arg Ser
1               5                   10


<210> SEQ ID NO 16
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 16

Val Asp Thr Tyr Asp Gly Arg Gly Asp Ser Val Val Tyr Gly Leu Arg
1               5                   10                  15

Ser


<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Arg Gly Asp Ser Leu Ala Tyr Gly Leu Arg Ser
1               5                   10


<210> SEQ ID NO 18
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 18

Val Asp Thr Tyr Asp Gly Arg Gly Asp Ser Leu Ala Tyr Gly Leu Arg
1               5                   10                  15

Ser


<210> SEQ ID NO 19
<211> LENGTH: 116
<212> TYPE: PRT
<213> ORGANISM: Mouse

<400> SEQUENCE: 19

Gln Val Gln Leu Gln Gln Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
```

-continued

```
            20                  25                  30

Glu Met His Trp Val Lys Gln Thr Pro Val His Gly Leu Glu Trp Ile
        35                  40                  45

Gly Ala Ile His Pro Gly Arg Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Ile Thr Gly Tyr Phe Asp Val Trp Gly Ala Gly Thr Thr Val
            100                 105                 110

Thr Val Ser Ser
        115


<210> SEQ ID NO 20
<211> LENGTH: 113
<212> TYPE: PRT
<213> ORGANISM: Mouse

<400> SEQUENCE: 20

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg


<210> SEQ ID NO 21
<211> LENGTH: 5
<212> TYPE: PRT
<213> ORGANISM: Mouse

<400> SEQUENCE: 21

Asp Tyr Glu Met His
1               5


<210> SEQ ID NO 22
<211> LENGTH: 17
<212> TYPE: PRT
<213> ORGANISM: Mouse

<400> SEQUENCE: 22

Ala Ile His Pro Gly Arg Gly Gly Thr Ala Tyr Asn Gln Lys Phe Lys
1               5                   10                  15

Gly


<210> SEQ ID NO 23
<211> LENGTH: 7
<212> TYPE: PRT
```

-continued

<213> ORGANISM: Mouse

<400> SEQUENCE: 23

Ile Thr Gly Tyr Phe Asp Val
1 5

<210> SEQ ID NO 24
<211> LENGTH: 16
<212> TYPE: PRT
<213> ORGANISM: Mouse

<400> SEQUENCE: 24

Arg Ser Ser Gln Ser Ile Val His Ser Asn Gly Asn Thr Tyr Leu Glu
1 5 10 15

<210> SEQ ID NO 25
<211> LENGTH: 7
<212> TYPE: PRT
<213> ORGANISM: Mouse

<400> SEQUENCE: 25

Lys Val Ser Asn Arg Phe Ser
1 5

<210> SEQ ID NO 26
<211> LENGTH: 9
<212> TYPE: PRT
<213> ORGANISM: Mouse

<400> SEQUENCE: 26

Phe Gln Gly Ser His Val Pro Leu Thr
1 5

<210> SEQ ID NO 27
<211> LENGTH: 441
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (20)..(424)

<400> SEQUENCE: 27

```
cacgaagctt gccgccacc atg gac tgg acc tgg cgc gtg ttt tgc ctg ctc      52
                     Met Asp Trp Thr Trp Arg Val Phe Cys Leu Leu
                     1               5                   10

gcc gtg gct cct ggg gcc cac agc cag gtg cag ctg gtg cag tct ggg      100
Ala Val Ala Pro Gly Ala His Ser Gln Val Gln Leu Val Gln Ser Gly
            15                  20                  25

gct gag gtg aag aag cct ggg tcc tcc gtg aag gtc tcc tgc aag gct      148
Ala Glu Val Lys Lys Pro Gly Ser Ser Val Lys Val Ser Cys Lys Ala
        30                  35                  40

tct gga ggt acc ttc agc gac tat gaa atg cac tgg gtg cga cag gcc      196
Ser Gly Gly Thr Phe Ser Asp Tyr Glu Met His Trp Val Arg Gln Ala
    45                  50                  55

cct gga caa ggg ctt gag tgg atg gga gct att cat cca gga aga ggt      244
Pro Gly Gln Gly Leu Glu Trp Met Gly Ala Ile His Pro Gly Arg Gly
60                  65                  70                  75

ggt act gcc tac aat cag aag ttc aag ggc aga gtc acg att acc gcg      292
Gly Thr Ala Tyr Asn Gln Lys Phe Lys Gly Arg Val Thr Ile Thr Ala
                80                  85                  90

gac aaa tcc act agt aca gcc tac atg gag ctg agc agc ctg aga tct      340
Asp Lys Ser Thr Ser Thr Ala Tyr Met Glu Leu Ser Ser Leu Arg Ser
```

-continued

```
         95                  100                 105

gag gac acg gcc gtg tat tac tgt gcg aga att act ggg tac ttc gat      388
Glu Asp Thr Ala Val Tyr Tyr Cys Ala Arg Ile Thr Gly Tyr Phe Asp
        110                 115                 120

gtc tgg ggg caa ggg acc acg gtc acc gtc tcc tca ggtgagtgga           434
Val Trp Gly Gln Gly Thr Thr Val Thr Val Ser Ser
    125                 130                 135

tccgcga                                                              441


<210> SEQ ID NO 28
<211> LENGTH: 135
<212> TYPE: PRT
<213> ORGANISM: Artificial Sequence
<220> FEATURE:
<223> OTHER INFORMATION: Synthetic Construct

<400> SEQUENCE: 28

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Asp Tyr Glu Met His Trp Val Arg Gln Ala Pro Gly Gln Gly Leu
    50                  55                  60

Glu Trp Met Gly Ala Ile His Pro Gly Arg Gly Gly Thr Ala Tyr Asn
65                  70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ile Thr Gly Tyr Phe Asp Val Trp Gly Gln Gly
        115                 120                 125

Thr Thr Val Thr Val Ser Ser
    130                 135


<210> SEQ ID NO 29
<211> LENGTH: 455
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (20)..(415)

<400> SEQUENCE: 29

cacgaagctt gccgccacc atg gga tgg agc tgt atc atc ctc ttc ttg gta      52
                     Met Gly Trp Ser Cys Ile Ile Leu Phe Leu Val
                     1               5                   10

gca aca gct aca ggt gtc cac tcc gat gtt gtg atg act cag tct cca      100
Ala Thr Ala Thr Gly Val His Ser Asp Val Val Met Thr Gln Ser Pro
            15                  20                  25

ctc tcc ctg ccc gtc acc ctt gga cag ccg gcc tcc atc tcc tgc agg      148
Leu Ser Leu Pro Val Thr Leu Gly Gln Pro Ala Ser Ile Ser Cys Arg
        30                  35                  40

agc tct caa agc att gta cat agt aat gga aac acc tat ttg gaa tgg      196
Ser Ser Gln Ser Ile Val His Ser Asn Gly Asn Thr Tyr Leu Glu Trp
    45                  50                  55

tac ctg cag aag cca ggg cag tct cca cag ctc ctg atc tat aaa gtt      244
```

-continued

```
Tyr Leu Gln Lys Pro Gly Gln Ser Pro Gln Leu Leu Ile Tyr Lys Val
60                  65                  70                  75

tcc aac cga ttt tct ggg gtc cca gac aga ttc agc ggc agt ggg tca      292
Ser Asn Arg Phe Ser Gly Val Pro Asp Arg Phe Ser Gly Ser Gly Ser
                80                  85                  90

ggc act gat ttc aca ctg aaa atc agc agg gtt gaa gct gaa gac gtc      340
Gly Thr Asp Phe Thr Leu Lys Ile Ser Arg Val Glu Ala Glu Asp Val
            95                  100                 105

gga gtt tat tac tgc ttt caa ggt tca cat gtt ccg ctc acg ttt ggc      388
Gly Val Tyr Tyr Cys Phe Gln Gly Ser His Val Pro Leu Thr Phe Gly
        110                 115                 120

cag ggg acc aag ctg gag atc aaa cgt gagtagaatt taaactttgc            435
Gln Gly Thr Lys Leu Glu Ile Lys Arg
    125                 130

ttcctcagtt ggatccgcga                                                455


<210> SEQ ID NO 30
<211> LENGTH: 132
<212> TYPE: PRT
<213> ORGANISM: Artificial Sequence
<220> FEATURE:
<223> OTHER INFORMATION: Synthetic Construct

<400> SEQUENCE: 30

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Leu Gly Gln Pro Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Gly Ser His Val Pro Leu Thr Phe Gly Gln Gly Thr Lys Leu
        115                 120                 125

Glu Ile Lys Arg
    130


<210> SEQ ID NO 31
<211> LENGTH: 97
<212> TYPE: DNA
<213> ORGANISM: Artificial Sequence
<220> FEATURE:
<223> OTHER INFORMATION: Synthetic DNA

<400> SEQUENCE: 31

cacgaagctt gccgccacca tggactggac ctggcgcgtg ttttgcctgc tcgccgtggc     60

tcctggggcc cacagccagg tgcagctggt gcagtct                               97


<210> SEQ ID NO 32
<211> LENGTH: 88
<212> TYPE: DNA
<213> ORGANISM: Artificial Sequence
<220> FEATURE:
<223> OTHER INFORMATION: Synthetic DNA
```

-continued

<400> SEQUENCE: 32
tcgctgaagg tacctccaga agccttgcag gagaccttca cggaggaccc aggcttcttc 60
acctcagccc cagactgcac cagctgca 88

<210> SEQ ID NO 33
<211> LENGTH: 103
<212> TYPE: DNA
<213> ORGANISM: Artificial Sequence
<220> FEATURE:
<223> OTHER INFORMATION: Synthetic DNA

<400> SEQUENCE: 33
ttctggaggt accttcagcg actatgaaat gcactgggtg cgacaggccc ctggacaagg 60
gcttgagtgg atgggagcta ttcatccagg aagaggtggt act 103

<210> SEQ ID NO 34
<211> LENGTH: 90
<212> TYPE: DNA
<213> ORGANISM: Artificial Sequence
<220> FEATURE:
<223> OTHER INFORMATION: Synthetic DNA

<400> SEQUENCE: 34
catgtaggct gtactagtgg atttgtccgc ggtaatcgtg actctgccct tgaacttctg 60
attgtaggca gtaccacctc ttcctggatg 90

<210> SEQ ID NO 35
<211> LENGTH: 95
<212> TYPE: DNA
<213> ORGANISM: Artificial Sequence
<220> FEATURE:
<223> OTHER INFORMATION: Synthetic DNA

<400> SEQUENCE: 35
tccactagta cagcctacat ggagctgagc agcctgagat ctgaggacac ggccgtgtat 60
tactgtgcga gaattactgg gtacttcgat gtctg 95

<210> SEQ ID NO 36
<211> LENGTH: 69
<212> TYPE: DNA
<213> ORGANISM: Artificial Sequence
<220> FEATURE:
<223> OTHER INFORMATION: Synthetic DNA

<400> SEQUENCE: 36
tcgcggatcc actcacctga ggagacggtg accgtggtcc cttgccccca gacatcgaag 60
tacccagta 69

<210> SEQ ID NO 37
<211> LENGTH: 40
<212> TYPE: DNA
<213> ORGANISM: Artificial Sequence
<220> FEATURE:
<223> OTHER INFORMATION: Synthetic DNA

<400> SEQUENCE: 37
cacgaagctt gccgccacca tggactggac ctggcgcgtg 40

<210> SEQ ID NO 38
<211> LENGTH: 40
<212> TYPE: DNA

-continued

<213> ORGANISM: Artificial Sequence
<220> FEATURE:
<223> OTHER INFORMATION: Synthetic DNA

<400> SEQUENCE: 38
tcgcggatcc actcacctga ggagacggtg accgtggtcc 40

<210> SEQ ID NO 39
<211> LENGTH: 82
<212> TYPE: DNA
<213> ORGANISM: Artificial Sequence
<220> FEATURE:
<223> OTHER INFORMATION: Synthetic DNA

<400> SEQUENCE: 39
cacgaagctt gccgccacca tgggatggag ctgtatcatc ctcttcttgg tagcaacagc 60
tacaggtgtc cactccgatg tt 82

<210> SEQ ID NO 40
<211> LENGTH: 102
<212> TYPE: DNA
<213> ORGANISM: Artificial Sequence
<220> FEATURE:
<223> OTHER INFORMATION: Synthetic DNA

<400> SEQUENCE: 40
aatgctttga gagctcctgc aggagatgga ggccggctgt ccaagggtga cgggcaggga 60
gagtggagac tgagtcatca caacatcgga gtggacacct gt 102

<210> SEQ ID NO 41
<211> LENGTH: 113
<212> TYPE: DNA
<213> ORGANISM: Artificial Sequence
<220> FEATURE:
<223> OTHER INFORMATION: Synthetic DNA

<400> SEQUENCE: 41
tgcaggagct ctcaaagcat tgtacatagt aatggaaaca cctatttgga atggtacctg 60
cagaagccag ggcagtctcc acagctcctg atctataaag tttccaaccg att 113

<210> SEQ ID NO 42
<211> LENGTH: 114
<212> TYPE: DNA
<213> ORGANISM: Artificial Sequence
<220> FEATURE:
<223> OTHER INFORMATION: Synthetic DNA

<400> SEQUENCE: 42
tccgacgtct tcagcttcaa ccctgctgat tttcagtgtg aaatcagtgc ctgacccact 60
gccgctgaat ctgtctggga ccccagaaaa tcggttggaa actttataga tcag 114

<210> SEQ ID NO 43
<211> LENGTH: 64
<212> TYPE: DNA
<213> ORGANISM: Artificial Sequence
<220> FEATURE:
<223> OTHER INFORMATION: Synthetic DNA

<400> SEQUENCE: 43
gttgaagctg aagacgtcgg agtttattac tgctttcaag gttcacatgt tccgctcacg 60
tttg 64

-continued

<210> SEQ ID NO 44
<211> LENGTH: 90
<212> TYPE: DNA
<213> ORGANISM: Artificial Sequence
<220> FEATURE:
<223> OTHER INFORMATION: Synthetic DNA

<400> SEQUENCE: 44
tcgcggatcc aactgaggaa gcaaagttta aattctactc acgtttgatc tccagcttgg 60
tcccctggcc aaacgtgagc ggaacatgtg 90

<210> SEQ ID NO 45
<211> LENGTH: 40
<212> TYPE: DNA
<213> ORGANISM: Artificial Sequence
<220> FEATURE:
<223> OTHER INFORMATION: Synthetic DNA

<400> SEQUENCE: 45
cacgaagctt gccgccacca tgggatggag ctgtatcatc 40

<210> SEQ ID NO 46
<211> LENGTH: 40
<212> TYPE: DNA
<213> ORGANISM: Artificial Sequence
<220> FEATURE:
<223> OTHER INFORMATION: Synthetic DNA

<400> SEQUENCE: 46
ctcgcggatc caactgagga agcaaagttt aaattctact 40

<210> SEQ ID NO 47
<211> LENGTH: 40
<212> TYPE: DNA
<213> ORGANISM: Artificial Sequence
<220> FEATURE:
<223> OTHER INFORMATION: Synthetic DNA

<400> SEQUENCE: 47
ttcgaagctt gccgccacca tggaatggag ctggatcttt 40

<210> SEQ ID NO 48
<211> LENGTH: 35
<212> TYPE: DNA
<213> ORGANISM: Artificial Sequence
<220> FEATURE:
<223> OTHER INFORMATION: Synthetic DNA

<400> SEQUENCE: 48
gaagatctgg atccactcac ctgaggaaac tgtga 35

<210> SEQ ID NO 49
<211> LENGTH: 39
<212> TYPE: DNA
<213> ORGANISM: Artificial Sequence
<220> FEATURE:
<223> OTHER INFORMATION: Synthetic DNA

<400> SEQUENCE: 49
cttaagcttg ccgccaccat gaagttgcct gttaggctg 39

<210> SEQ ID NO 50
<211> LENGTH: 36
<212> TYPE: DNA
<213> ORGANISM: Artificial Sequence
<220> FEATURE:

-continued

```
<223> OTHER INFORMATION: Synthetic DNA

<400> SEQUENCE: 50

ctagatctgg atccacttac gtttcagctc cagctt                      36
```